(12) United States Patent
Yamada et al.

(10) Patent No.: US 10,436,629 B2
(45) Date of Patent: Oct. 8, 2019

(54) MEASUREMENT SYSTEM FOR MEASURING WEIGHT

(71) Applicant: Kitagawa Industries Co., Ltd., Aichi (JP)

(72) Inventors: Kazuki Yamada, Toki (JP); Lu Zhao, Nagoya (JP); Yasuo Kondo, Toyota (JP)

(73) Assignee: Kitagawa Industries Co., Ltd., Aichi (JP)

(*) Notice: Subject to any disclaimer, the term of this patent is extended or adjusted under 35 U.S.C. 154(b) by 135 days.

(21) Appl. No.: 15/461,445

(22) Filed: Mar. 16, 2017

(65) Prior Publication Data
US 2017/0268923 A1    Sep. 21, 2017

(30) Foreign Application Priority Data

Mar. 17, 2016  (JP) ................. 2016-054141

(51) Int. Cl.
| | |
|---|---|
| *G01G 19/44* | (2006.01) |
| *G01G 21/28* | (2006.01) |
| *A61B 5/103* | (2006.01) |
| *A61B 5/00* | (2006.01) |
| *A43B 3/00* | (2006.01) |
| *A43B 17/00* | (2006.01) |

(52) U.S. Cl.
CPC ............ *G01G 19/44* (2013.01); *A61B 5/103* (2013.01); *A61B 5/1038* (2013.01); *A61B 5/6802* (2013.01); *A61B 5/6807* (2013.01); *G01G 21/28* (2013.01); *A43B 3/0005* (2013.01); *A43B 17/00* (2013.01); *A61B 2562/0219* (2013.01); *A61B 2562/0247* (2013.01)

(58) Field of Classification Search
CPC ........... G01L 1/24; G01L 1/247; G01L 25/00; G01G 19/44; G01G 21/28
See application file for complete search history.

(56) References Cited

U.S. PATENT DOCUMENTS

| | | | |
|---|---|---|---|
| 7,771,371 B2 * | 8/2010 | Avni ................. | G01L 5/008 600/592 |
| 10,070,680 B2 * | 9/2018 | Molyneux ................ | A43B 3/00 |
| 2003/0009308 A1 * | 1/2003 | Kirtley ................. | A61B 5/1038 702/141 |

(Continued)

FOREIGN PATENT DOCUMENTS

JP    2012057969 A    3/2012

*Primary Examiner* — Natalie Huls
(74) *Attorney, Agent, or Firm* — Jenkins, Wilson, Taylor & Hunt, P.A.

(57) ABSTRACT

A measurement information output system comprises an input unit and an output unit. The input unit is configured to input, to an arithmetic unit, a detected force value indicating the magnitude of force detected by one or more force sensors arranged so as to receive impact by motion of a measurement target and a detected acceleration value indicating the acceleration of the measurement target detected by an acceleration sensor arranged so as to detect the acceleration of the measurement target. The arithmetic unit is configured to compute the weight of the measurement target on the basis of the detected force value and the detected acceleration value. The output unit is configured to output, as a measured weight value, the weight of the measurement target computed by the arithmetic unit.

16 Claims, 16 Drawing Sheets

(56) References Cited

U.S. PATENT DOCUMENTS

| | | | | |
|---|---|---|---|---|
| 2003/0097878 | A1* | 5/2003 | Farringdon | A61B 5/1038 73/819 |
| 2003/0163287 | A1* | 8/2003 | Vock | A43B 3/0005 702/187 |
| 2006/0143645 | A1* | 6/2006 | Vock | A43B 3/00 725/9 |
| 2007/0068244 | A1* | 3/2007 | Billing | A61B 5/1038 73/172 |
| 2007/0084642 | A1* | 4/2007 | Maxi | A43B 3/0005 177/132 |
| 2008/0264141 | A1* | 10/2008 | Kenmochi | G01G 3/1414 73/1.08 |
| 2009/0038182 | A1* | 2/2009 | Lans | A43B 3/0005 36/136 |
| 2009/0137933 | A1* | 5/2009 | Lieberman | A61B 5/1036 600/595 |
| 2010/0211355 | A1* | 8/2010 | Horst | A61B 5/1038 702/173 |
| 2011/0054359 | A1* | 3/2011 | Sazonov | A43B 3/0005 600/595 |
| 2011/0153261 | A1* | 6/2011 | Jang | A43B 3/0005 702/141 |
| 2011/0214501 | A1* | 9/2011 | Ross | A43B 3/0005 73/172 |
| 2014/0174205 | A1* | 6/2014 | Clarke | A61B 5/1038 73/862.626 |
| 2014/0326085 | A1* | 11/2014 | Lee | A61B 5/6829 73/865.4 |
| 2015/0075879 | A1* | 3/2015 | Sakai | G01G 21/00 177/1 |
| 2015/0100251 | A1* | 4/2015 | Solinsky | G01C 21/005 702/33 |
| 2015/0182844 | A1* | 7/2015 | Jang | G01G 19/50 700/91 |
| 2015/0359457 | A1* | 12/2015 | Blumenthal | A63F 13/06 73/172 |
| 2015/0359460 | A1* | 12/2015 | Rubin | A43B 17/00 702/175 |
| 2016/0011091 | A1* | 1/2016 | Huang | G01N 3/24 73/841 |
| 2016/0022143 | A1* | 1/2016 | Gray | A61B 5/0004 340/870.07 |
| 2016/0313174 | A1* | 10/2016 | Lightstone | G01G 19/50 |
| 2017/0038243 | A1* | 2/2017 | Peng | G01G 3/13 |
| 2018/0003547 | A1* | 1/2018 | Ten Kate | G01G 19/44 |

\* cited by examiner

MEASUREMENT SYSTEM FOR MEASURING WEIGHT

CROSS-REFERENCE TO RELATED APPLICATIONS

This application claims the benefit of Japanese Patent Application No. 2016-054141 filed on Mar. 17, 2016 with the Japan Patent Office, the entire disclosure of which is incorporated herein by reference.

BACKGROUND

The present disclosure relates to a system which outputs measurement information.

Conventionally, a system which measures a weight and outputs a measurement value of the weight is known. For example, a body weight measurement system which measures a body weight by using a load cell as a load sensor and outputs a measurement value of the weight is known (see, for example, Japanese Unexamined Patent Application Publication No. 2012-057969A).

SUMMARY

A measurement system which uses a load cell measures a weight by taking advantage of distortion which occurs at a portion which receives a load. The load cell is composed of a hard member to accurately detect the distortion due to a load and precisely measure a weight. For the same reason, a weight scale is installed on a hard floor surface to measure a weight by using the load cell. The measurement is performed in a state where a measurement target is still with respect to the weight scale. Thus, the conventional weight measurement requires the measurement target to be still, and is significantly restricted by measurement environment. In other words, the conventional measurement system has been less convenient for users.

Hence, according to one aspect of the present disclosure, it is desirable to provide a highly convenient and new weight measuring technique.

A measurement information output system according to an aspect of the present disclosure includes an input unit and an output unit. This measurement information output system carries out a process using one or more force sensors arranged so as to receive impact generated by motion of a measurement target and an acceleration sensor arranged so as to detect acceleration of the measurement target.

The input unit is configured to input a detected force value indicating magnitude of force detected by the one or more force sensors and a detected acceleration value indicating acceleration of the measurement target detected by the acceleration sensor, into an arithmetic unit configured to compute weight of the measurement target, based on the detected force value and the detected acceleration value. The output unit is configured to output, as a measured weight value, the weight of the measurement target computed by the arithmetic unit.

According to an aspect of the present disclosure, the measurement information output system may include an arithmetic unit configured to compute the weight of the measurement target, based on the detected force value and the detected acceleration value input from the input unit.

With this measurement information output system, it is possible to output a result obtained by computing the weight of the measurement target on the basis of the magnitude of force resulting from impact generated by motion of the measurement target and corresponding acceleration. Hence, with this measurement information output system, it is possible to measure the weight of the measurement target even when the measurement target is not standing still, which enables accurate weight measurement with little restrictions relating to measurement environment. Hence, it is possible to provide a new, highly convenient weight measurement system.

According to an aspect of the present disclosure, the measurement information output system may include the one or more force sensors or may include the acceleration sensor.

The weight of the measurement target may be body weight of a measurement target person. According to an aspect of the present disclosure, the input unit may be configured to input, as the detected force value, a detected force value indicating magnitude of force detected by one or more force sensors arranged so as to support the measurement target person and receive impact generated by motion of the measurement target person, into the arithmetic unit.

The input unit may be configured to input, as the detected acceleration value, a detected acceleration value indicating acceleration of the measurement target person detected by an acceleration sensor arranged so as to move together with the measurement target person, into the arithmetic unit. According to this measurement information output system, the user does not need to perform an action of standing still on a scale as in a known case, for weight measurement.

The one or more force sensors may be one or more force sensors arranged in a portion, supporting body weight of the measurement target person, of footwear put on a foot of the measurement target person. According to this measurement information output system using the one or more force sensors, it is possible to output a measurement value of the body weight of the user by using the detected force value and the detected acceleration value obtained at the time of the user moving with the footwear.

The measurement information output system may include, as the one or more force sensors, force sensors arranged in respective pieces of a pair of footwear put on both feet of the measurement target person. The body weight measurement using force sensors provided to both feet can enable more highly accurate body weight measurement than body weight measurement using a force sensor provided for one of the feet.

The arithmetic unit may be configured to compute the weight of the measurement target on the basis of the detected force value and the detected acceleration value in a period in which change of the detected acceleration value satisfies a prescribed condition. The change of the detected acceleration value represents characteristics corresponding to the motion state of the measurement target. For this reason, by computing the weight as described above, it is possible to compute the weight on the basis of the detected force value and the detected acceleration value in a motion state suitable for weight computation.

The arithmetic unit may be configured to compute the weight of the measurement target on the basis of the greatest value of the detected acceleration value in a period satisfying a prescribed condition and the detected force value indicating magnitude of force detected by the force sensor when the greatest value is detected. The arithmetic unit may be configured to compute the weight of the measurement target on the basis of the greatest value of the detected acceleration value in a period satisfying a prescribed condition and the greatest value of the detected force value in the period. According to this configuration, it is possible to compute the weight of the measurement target highly accurately.

The period satisfying the prescribed condition may be a certain period after a measurement instruction is input via a user interface. For example, when an environment in which the measurement target performs a specific motion after the measurement instruction is assumed, the arithmetic unit can compute a weight highly accurately on the basis of the detected force value relating to the impact generated by the specific motion and the corresponding detected acceleration value. Alternatively, the period satisfying the prescribed condition may be a period in which change of the detected acceleration value satisfies a prescribed condition, after a measurement instruction is input via a user interface.

The measurement information output system may include an instruction unit instructing performing of the specific motion. In this case, the period satisfying the prescribed condition may be a period in which the specific motion is performed in response to the instruction by the instruction unit.

The arithmetic unit may be configured to compute a statistical representative value of the weight by performing statistical processing on a group of the weights computed by repeatedly carrying out a process of computing the weight. Examples of the representative value include an average value and a median. The output unit may be configured to output, as a measurement value of weight, the representative value computed by the arithmetic unit.

The measurement information output system may include a storage unit storing a correction parameter.

The correction parameter may be used to correct the detected force value. The correction parameter may be a correction parameter for correcting the detected force value to the value indicating the magnitude of force obtained by assuming that the force sensor receives the total weight of the measurement target.

The arithmetic unit may be configured to compute, as the weight of the measurement target, weight based on the detected force value obtained by correcting the detected force value input from the input unit by using the correction parameter stored in the storage unit, and the detected acceleration value. Through this correction, it is possible to perform further accurate weight measurement.

The measurement information output system may be configured to include a storage unit storing a correction parameter, an acquisition unit acquiring an initial value of the weight of the measurement target, and an initial processing unit computing the correction parameter and storing the correction parameter in the storage unit.

The initial processing unit may be configured to compute, as the correction parameter to be stored in the storage unit, the correction parameter used to compute the weight corresponding to the initial value by the arithmetic unit, on the basis of the initial value acquired by the acquisition unit, and the detected force value and the detected acceleration value input from the input unit. By using the correction parameter thus computed, it is possible to perform further accurate weight measurement.

According to an aspect of the present disclosure, provided may be a measurement information output system including one or more force sensors arranged so as to receive impact generated by motion of a measurement target, an acceleration sensor arranged so as to detect acceleration of the measurement target, an arithmetic unit configured to compute weight of the measurement target on the basis of magnitude of force detected by the one or more force sensors and acceleration of the measurement target detected by the acceleration sensor, and an output unit configured to output the weight of the measurement target computed by the arithmetic unit, as a measurement value of the weight.

According to an aspect of the present disclosure, provided may be a program for causing a computer to execute at least one of a process of acquiring a detected force value indicating magnitude of force detected by one or more force sensors arranged so as to receive impact by motion of a measurement target, a process of acquiring a detected acceleration value indicating acceleration of the measurement target detected by an acceleration sensor arranged so as to detect acceleration of the measurement target, and a process of computing weight of the measurement target on the basis of the detected force value and the detected acceleration value thus acquired. The program may be provided by being recorded in a non-transitory computer readable storage medium.

According to an aspect of the present disclosure, provided may be a method comprising acquiring a detected force value indicating magnitude of force detected by one or more force sensors arranged so as to receive impact by motion of a measurement target, acquiring a detected acceleration value indicating acceleration of the measurement target detected by an acceleration sensor arranged so as to detect acceleration of the measurement target, and computing weight of the measurement target on the basis of the detected force value and the detected acceleration value thus acquired.

DETAILED DESCRIPTION OF THE PREFERRED EMBODIMENTS

Embodiments of the present disclosure will be described below with reference to the drawings.

First Embodiment

Figure 1:
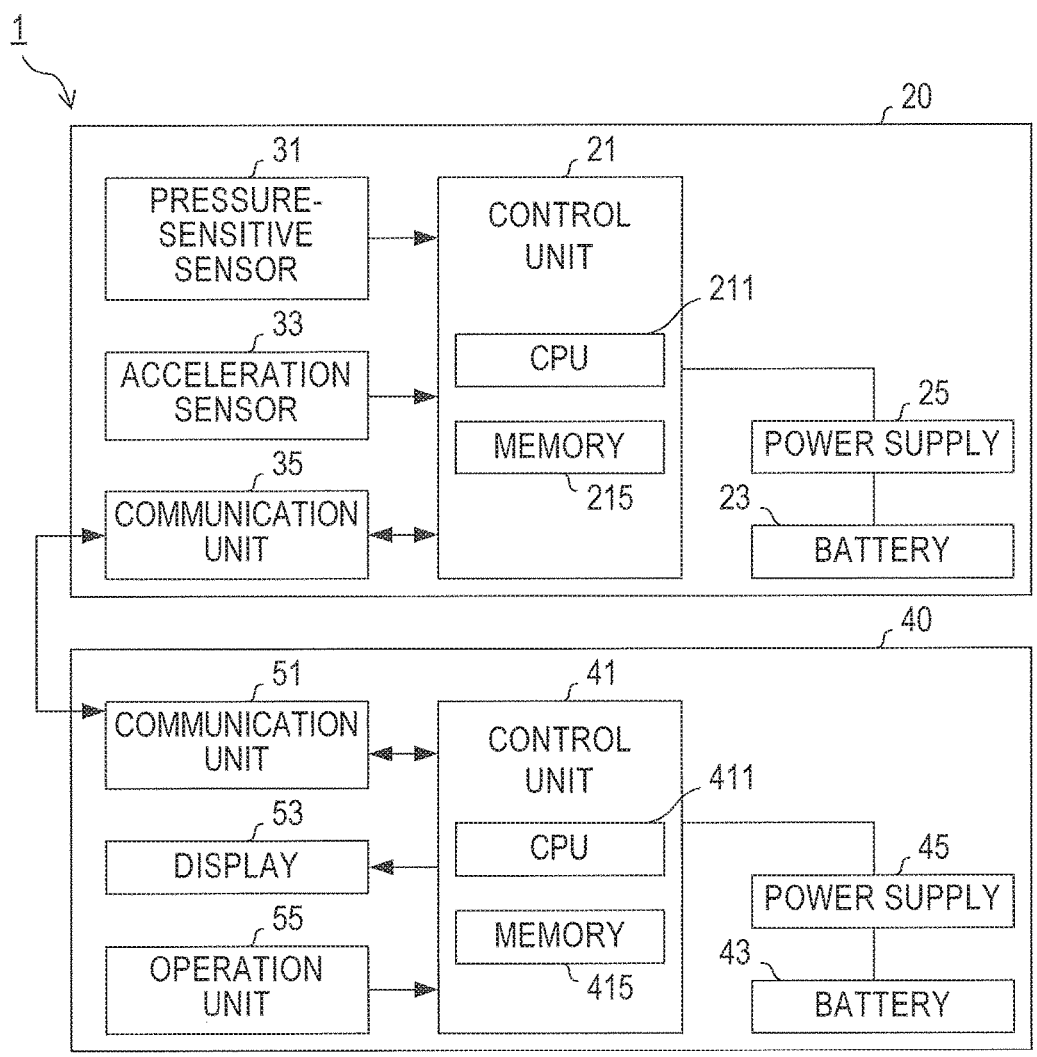
FIG. 1 is a block diagram illustrating a configuration of a measurement system according to a first embodiment.

A measurement system 1 according to the present embodiment illustrated in FIG. 1 is a system configured to measure and display the body weight of a user wearing a shoe-type wearable device 20.

The measurement system 1 includes a shoe-type wearable device 20 and a mobile communication terminal 40 possessed by the user wearing the shoe-type wearable device 20. The shoe-type wearable device 20 is attached to shoes 10 in an integrated or detachable manner. According to the present embodiment, the shoe-type wearable device 20 is attached to the shoe 10 put on a dominant foot of a user, of the pair of shoes 10 put on both feet of the user.

An example of the mobile communication terminal 40 is a smartphone or a different wearable device attached to the body of the user. Examples of the different wearable device include a watch-type wearable device and a glass-type wearable device.

As illustrated in FIG. 1, the shoe-type wearable device 20 includes a control unit 21, a battery 23, a power supply 25, a pressure-sensitive sensor 31, an acceleration sensor 33, and a communication unit 35.

The control unit 21 includes a central processing unit (CPU) 211 and a memory 215. The control unit 21 includes, as a memory 215, one or more of a random access memory (RAM), a read only memory (ROM), and a non-volatile RAM (NVRAM), into which data can be electrically rewritten. Examples of an NVRAM include a flash memory and an electrically erasable and programmable ROM (EEPROM).

The CPU 211 is configured to carry out a process according to a program stored in the memory 215. The process carried out by the CPU 211 will be described below as a process carried out by the control unit 21 or the shoe-type wearable device 20. The control unit 21 performs centralized control of the entire shoe-type wearable device 20 by carrying out the process according to the program. The control unit 21 operates by receiving power from the battery 23 via the power supply 25. The power supply 25 supplies power from the battery 23 to each of the units of the shoe-type wearable device 20.

Figure 2:
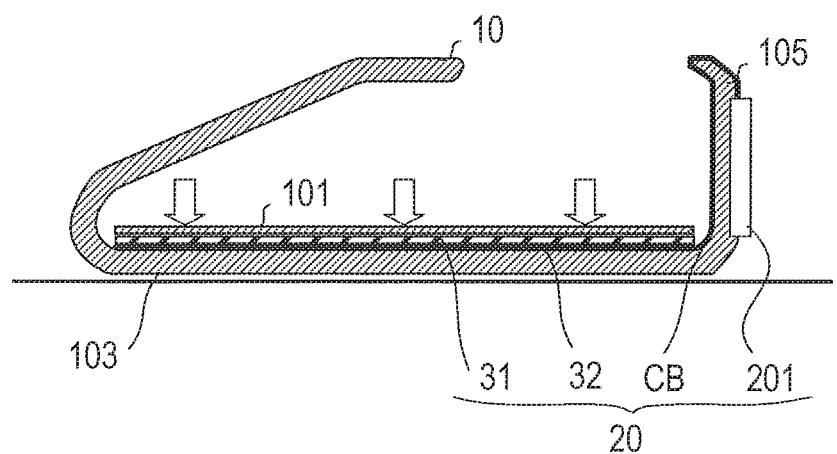
FIG. 2 is an explanatory view relating to an arrangement of a wearable device attached to a shoe.

As illustrated in FIG. 2, the pressure-sensitive sensor 31 is provided between a shoe insole 101 and a shoe sole 103 of the shoe 10 and arranged so as to receive the body weight of the user wearing the shoes 10 and thereby receive impact, from the foot, generated by walking. According to the example illustrated in FIG. 2, the pressure-sensitive sensor 31 is provided on almost the entire bottom surface of the shoe insole 101, which is in contact with the bottom of the foot of the user. The pressure-sensitive sensor 31 may be provided to a portion instead of the entire bottom surface, the portion being able to stably receive the impact.

The pressure-sensitive sensor 31 includes, for example, conductive rubber and is configured to detect the magnitude of force acting on the pressure-sensitive sensor 31, by the use of the phenomenon in which the electrical resistance of conductive rubber changes according to distortion. The pressure-sensitive sensor 31 outputs a signal corresponding to electrical resistance and can thus output a signal indicating the magnitude of the force acting on the pressure-sensitive sensor 31. The above-described magnitude of force detected by the pressure-sensitive sensor 31 is also referred to as a detected force value below.

The output signal of the pressure-sensitive sensor 31 is input to the control unit 21 in a main body case 201 via a base plate 32 and a cable CB extending from the base plate 32. According to FIG. 2, the main body case 201 of the shoe-type wearable device 20 is attached to an outer surface of a heel portion 105 of the shoe 10. The output signal of the pressure-sensitive sensor 31 is converted to a digital signal and then transmitted to a device connected to the shoe-type wearable device 20 via the communication unit 35 with wires or wirelessly.

The acceleration sensor 33 is provided in the main body case 201 of the shoe-type wearable device 20 and arranged so as to detect the acceleration corresponding to the motion of the foot of the user as the acceleration of the user. The acceleration sensor 33 inputs a signal representing the detected acceleration to the control unit 21. The acceleration detected by the acceleration sensor 33 is also referred to as a detected acceleration value below.

The acceleration sensor 33 is configured, for example, as a triaxial acceleration sensor, which is a kind of a micro electro mechanical systems (MEMS) sensor. In this case, the acceleration sensor 33 detects the acceleration in each of the X, Y, and Z axis directions that are orthogonal to each other. An output signal from the acceleration sensor 33 in this case indicates the acceleration on each of the axes. The output signal from the acceleration sensor 33 is converted to a digital signal and then transmitted to the device connected to the shoe-type wearable device 20 via the communication unit 35. When the acceleration sensor 33 is a triaxial acceleration sensor, the magnitude of acceleration to be expressed below should be understood as being equal to the magnitude (specifically, L2 norm) of the three-dimensional acceleration vector taking the accelerations on the respective axes as elements.

The communication unit 35 is configured by a communication interface capable of communicating with the mobile communication terminal 40. For example, the communication unit 35 is configured to be capable of Bluetooth (registered trademark) communication. However, the configuration of the communication unit 35 is not limited to this. The communication unit 35 can be configured to be capable of wire communication or wireless communication with the mobile communication terminal 40 in a direct or indirect method through at least one of near field communication, dedicated short range communication, and wide area communication.

Next, a process carried out by the control unit 21 for measurement of the body weight of the user will be described using FIG. 3. This process will be referred to also as a "shoe-side process" below. Upon receipt of a connection request from the mobile communication terminal 40, the control unit 21 starts the process illustrated in FIG. 3.

Figure 3:
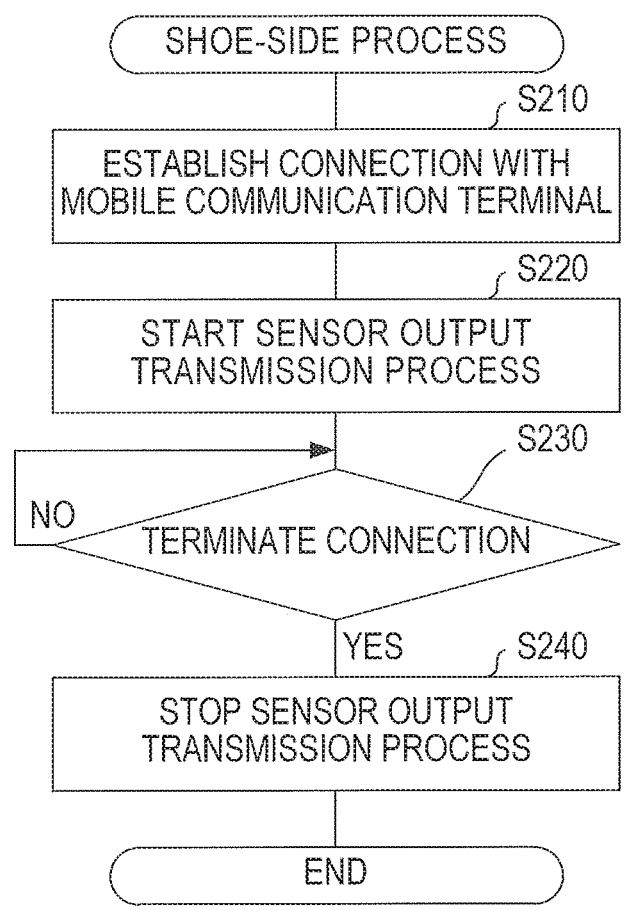
FIG. 3 is a flowchart illustrating a shoe-side process carried out by a control unit of the wearable device.

Upon start of the process presented in FIG. 3, the control unit 21 connects the device 20 itself to the mobile communication terminal 40 so as to be able to perform two-way communications (S210). The control unit 21 thereafter starts a sensor output transmission process (S220). Specifically, the control unit 21 starts a process of transmitting an output signal from the pressure-sensitive sensor 31 as a detected force signal to the above-described mobile communication terminal 40 via the communication unit 35 and also transmitting an output signal from the acceleration sensor 33 as a detected acceleration signal to the above-described mobile communication terminal 40 via the communication unit 35. The detected force signal and the detected acceleration signal will also be referred to as detection signals collectively below.

The control unit 21 continuously carries out the above-described started transmission of a detected force signal and a detected acceleration signal until the connection with the mobile communication terminal 40 is terminated. Upon the connection being terminated (Yes in S230), the control unit 21 terminates the transmission of the detection signals to the mobile communication terminal 40 (S240). In this way, the control unit 21 operates to transmit the output signals from the pressure-sensitive sensor 31 and the acceleration sensor 33 to the mobile communication terminal 40 while the connection with the mobile communication terminal 40 is maintained.

As illustrated in FIG. 1, the mobile communication terminal 40 connected to the shoe-type wearable device 20 so as to be able to communicate with the shoe-type wearable device 20 includes a control unit 41, a battery 43, a power supply 45, a communication unit 51, a display 53, and an operation unit 55. The mobile communication terminal 40 includes a hardware configuration as those of known smart-phones. Technical features of the mobile communication terminal 40 according to the present disclosure are implemented mainly by information processing based on a program.

The control unit 41 of the mobile communication terminal 40 includes a CPU 411 and a memory 415. The control unit 41 includes, as the memory 415, one or more of a RAM, a ROM, and a NVRAM. Examples of the NVRAM include a flash memory and an EEPROM.

The CPU 411 performs centralized control of the entire mobile communication terminal 40 by carrying out the process according to a program stored in the memory 415. The process carried out by the CPU 411 will be described below as a process carried out by the control unit 41 or the mobile communication terminal 40. The control unit 41 operates by receiving power from the battery 43 via the power supply 45. The power supply 45 is configured to supply power from the battery 43 to each of the units of the mobile communication terminal 40.

The communication unit 51 is configured to be able to communicate with the shoe-type wearable device 20 and is configured to input, to the control unit 41, the above-described detection signals transmitted from the shoe-type wearable device 20 that has established a connection with the communication unit 51.

The display 53 displays various kinds of information for the user under the control by the control unit 41. The display 53 is configured, for example, by a liquid crystal display. The operation unit 55 is a user interface that can receive operations and instructions from the user and is configured, for example, by a touch panel provided on the display 53.

A dedicated program (so-called App) for enabling body weight measurement and display using the shoe-type wearable device 20 is installed in the mobile communication terminal 40 thus configured. The control unit 41 carries out a process according to the installed program to thereby perform body weight measurement and display based on detection signals transmitted from the shoe-type wearable device 20.

Figure 4:
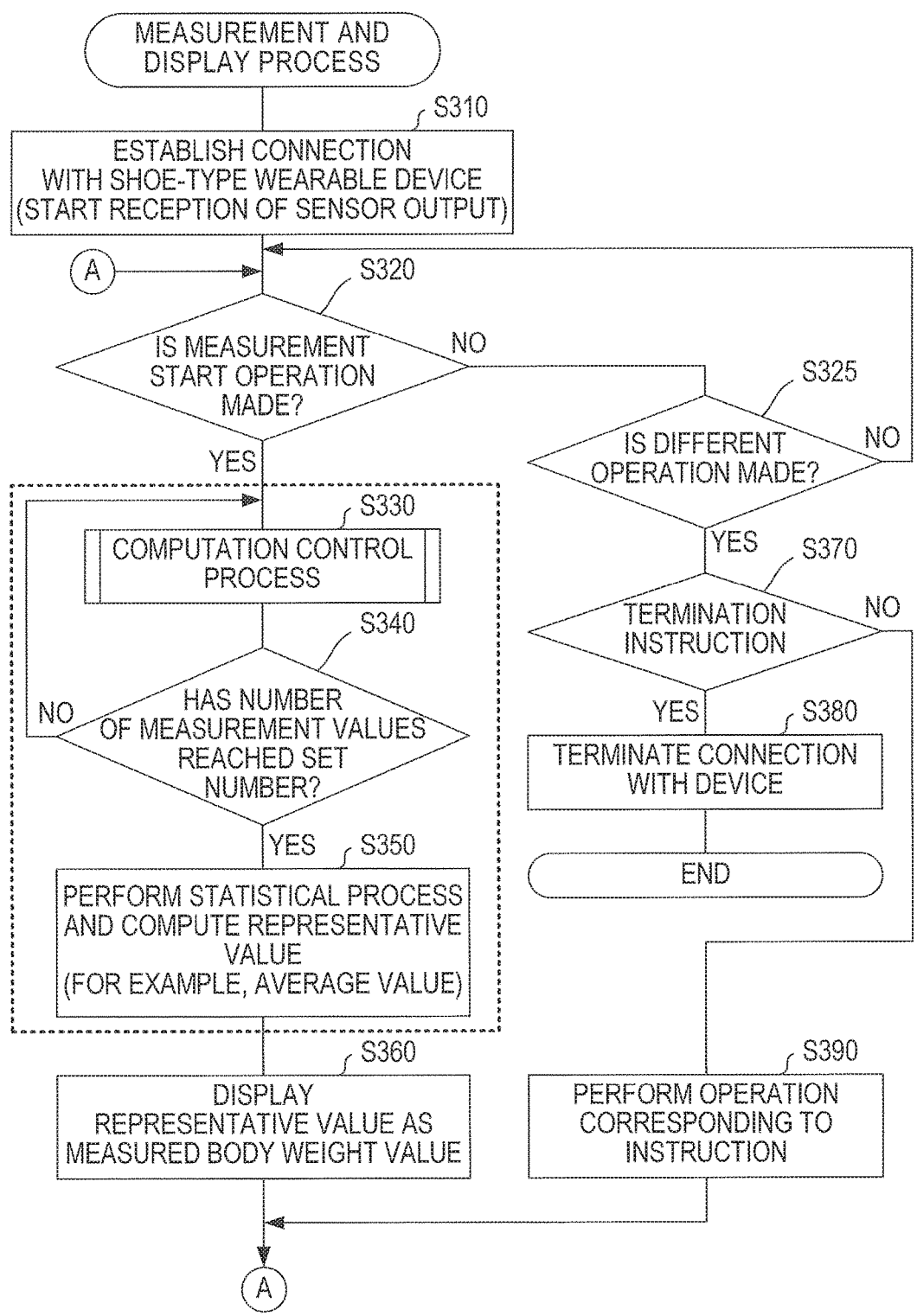
FIG. 4 is a flowchart illustrating a measurement and display process carried out by a control unit of a mobile communication terminal.

Upon receipt of an input of an instruction to execute the above-described dedicated program from the user via the operation unit 55, the control unit 41 starts a measurement and display process presented in FIG. 4. Upon start of the measurement and display process, the control unit 41 transmits a connection request to the shoe-type wearable device 20 that is registered in advance, to establish a connection with the shoe-type wearable device 20, and starts to receive, via the communication unit 51, detection signals transmitted from the shoe-type wearable device 20 (S310). Detection signals are continuously received while the connection with the shoe-type wearable device 20 is maintained.

After the reception is started, the control unit 41 receives operations from the user via the operation unit 55. To receive operations, the control unit 41 can display an operation window on the display 53. Upon input of an operation signal instructing to start measurement via the operation unit 55 (Yes in S320), the control unit 41 advances to S330.

Figure 5:
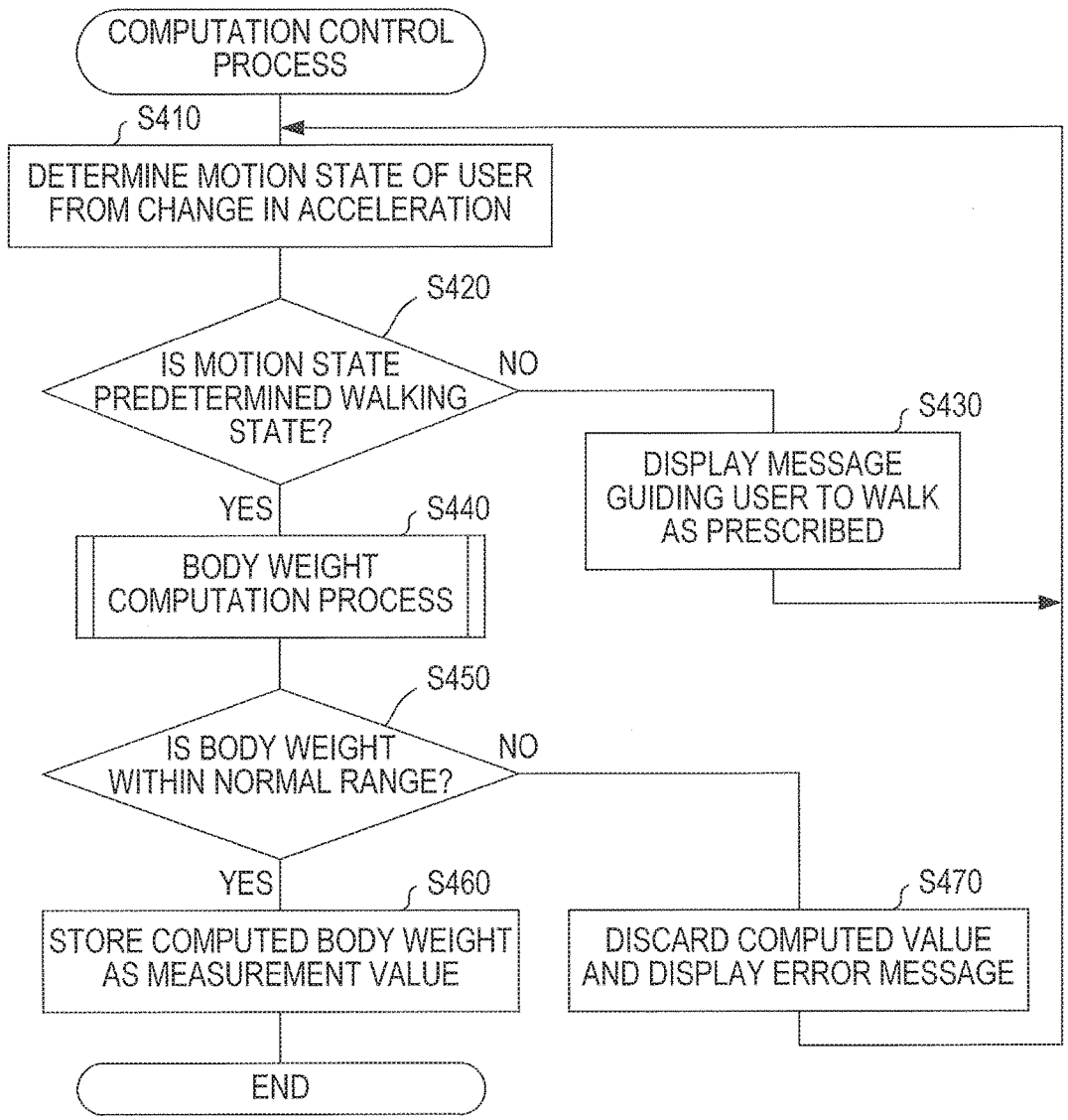
FIG. 5 is a flowchart illustrating a computation control process carried out by the control unit of the mobile communication terminal.

In S330, the control unit 41 carries out a computation control process presented in FIG. 5. Upon start of the computation control process, the control unit 41 determines the motion state of the user on the basis of a detected acceleration signal received from the shoe-type wearable device 20. Specifically, the control unit 41 determines whether the user is in a prescribed walking state, on the basis of the change in acceleration identified from the detected acceleration signal (S410).

The determination of a walking state is made to enable accurate body weight measurement with a limited motion state of the user at the time of body weight measurement. The determination of whether the user is in the prescribed walking state can be made on the basis of determination of whether the amount of change in acceleration per unit time is within a prescribed range. For example, it is possible to determine whether the user is currently in the prescribed walking state on the basis of whether, in a past certain period with the current time point as the end point, the greatest value or the average value of the amounts of change in acceleration per unit time that is sufficiently shorter than the past certain period is within the prescribed range. For this determination, the control unit 41 stores in advance the detected acceleration values of the time points indicated by respective received detected acceleration signals corresponding to a certain time period, in a RAM. When the change in acceleration is small, the user is assumed to be standing still. When the change in acceleration is large, the user is assumed to be running. Hence, on the basis of the above determination, it is possible to determine whether the user is walking at a walking speed within a prescribed range, as the prescribed walking state.

When it is determined that the user is not in the prescribed walking state (No in S420), the control unit 41 controls the display 53 to cause the display 53 to display, for the user, a message suggesting the user to walk in the prescribed walking state (S430). The control unit 41 thereafter advances to S410. In contrast, when it is determined that the motion state of the user is in the prescribed walking state (Yes in S420), the control unit 41 advances to S440 and carries out the body weight measurement process presented in FIG. 6.

Upon start of the body weight measurement process, the control unit 41 fetches, as observation data, the detected force value and the detected acceleration value at each of the time points indicated by detected force signals and detected acceleration signals in a certain time period (S510). The above-mentioned certain time period for which fetching is performed may be a certain time period after the start of the body weight computation process or may be the same time period as the time period for the detection of the acceleration used for the determination of the motion state of the user in S410 immediately before the start of the body weight computation process. The period for the detection of force and acceleration corresponding to the detected force values and the detected acceleration values indicated by the observation data is also referred to as an observation period below.

The control unit 41 thereafter identifies a greatest acceleration value Ap in the above-described observation period by referring to the above-described observation data (S520). The greatest acceleration value Ap expressed here is, when the acceleration sensor 33 is a triaxial acceleration sensor, the greatest value of the L2 norm of the above-described acceleration vector taking the accelerations of the respective axes as the elements.

Figure 7:
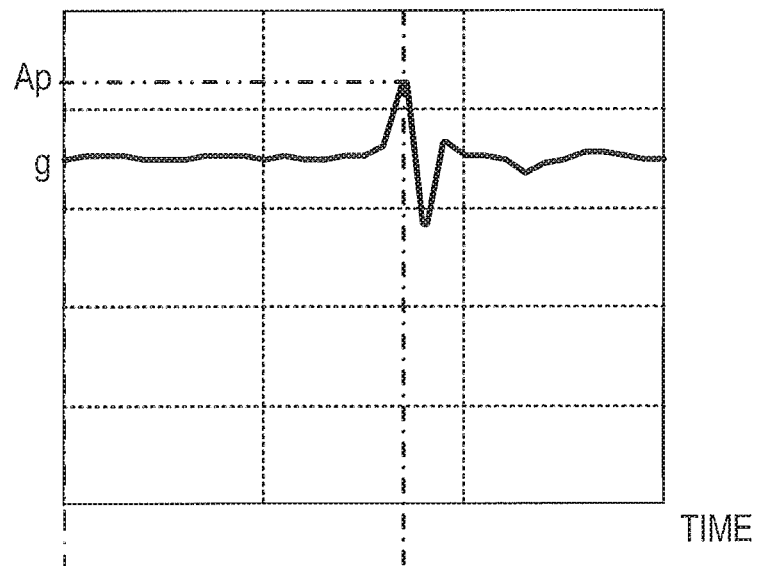
FIG. 7 is a diagram including a time versus acceleration graph in an upper part and a time versus force graph in a lower part.
Figure 7:
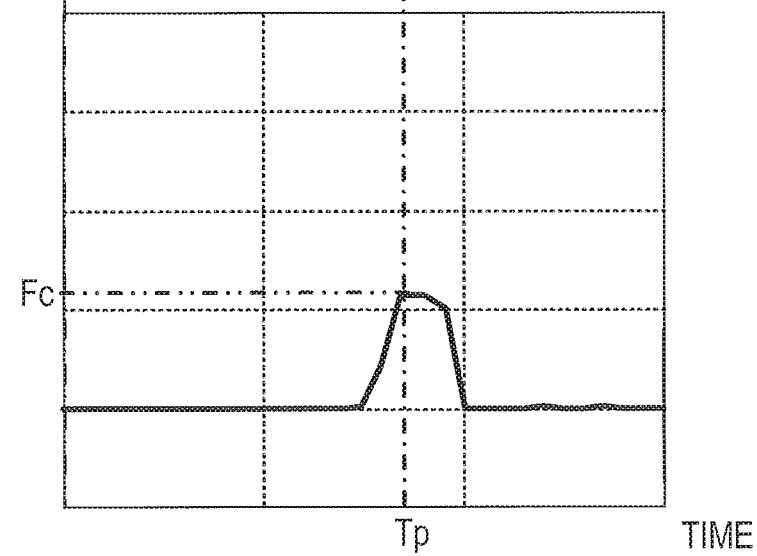

The upper part of FIG. 7 presents the greatest value Ap of the acceleration (L2 norm). The control unit 41 sequentially refers to the detected acceleration values in the observation period in chronological order and stores the greatest detection value (greatest L2 norm) among the detected acceleration values thus referred to, thereby being able to identify the detected acceleration value (L2 norm) that is stored finally as the greatest acceleration value Ap. According to the example presented in the upper part of FIG. 7, the acceleration sensor 33 detects the acceleration corresponding to gravity g even in a state where the user is standing still. An acceleration component resulting from motion of the user is detected in the manner of being added to the gravity g.

After the identification of the greatest acceleration value Ap, the control unit 41 identifies a detected force value Fc at a time point Tp at which this greatest acceleration value Ap is observed, on the basis of the above-described observation data (S530). The lower part of FIG. 7 presents the detected force value Fc at a time point Tp corresponding to the greatest value Ap. The greatest acceleration value Ap and the corresponding detected force value Fc identified in S520 and S530 correspond respectively to a value of the acceleration acting on the acceleration sensor 33 and magnitude of the force acting on the pressure-sensitive sensor 31 at the time point when the impact force and the acceleration are the greatest by the foot of the user coming down and reaching the ground.

The control unit 41 thereafter computes a body weight M of the user on the basis of the greatest acceleration value Ap identified in S520 and the detected force value Fc identified in S530, according to Equation (1) below (S540).

$$M = K^* Fc/Ap \qquad \text{Equation (1)}$$

The correction factor K used here is obtained by a test in advance and incorporated in the program. Alternatively, the correction factor K is stored in the memory 415, specifically, the NVRAM. The control unit 41 can compute the body weight M according to the above equation by referring to the correction factor K stored in the memory 415.

The correction factor K can be obtained by substituting, into Equation (1), a pair of the greatest acceleration value Ap and the corresponding detected force value Fc (Ap, Fc) obtained in the above-described walking state in an environment where the body weight M is known, together with the known body weight M. The engineer of the measurement system 1 collects learning data (Ap, Fc, M) necessary for the computation of the correction factor K by the cooperation of a plurality of people and performs statistical processing on the correction factors K obtained by substituting the learning data into Equation (1), to thereby be able to determine an appropriate value of the correction factor K to be used in S540. The correction factor K can be expressed as a correction parameter for correcting the detected force value Fc so that the detected force value Fc is to be equal to the value indicating the magnitude of force obtained by assuming that the pressure-sensitive sensor 31 receives the total weight of the user. In other words, the correction factor K can be expressed as a correction parameter for substituting the motion model of the foot into the motion model of the entire body.

It is understood that the body weight M can be calculated according to Equation (1) since the relation between the force F observed by the pressure-sensitive sensor 31 as a result of impact occurring when one of the feet of the user reaches the ground while the user is walking and the acceleration A of the moment is represented by the relational expression F=MA, on the assumption that the pressure-sensitive sensor 31 supports the entire body weight and the acceleration detected by the acceleration sensor 33 is the acceleration based on the motion of the entire body of the user. A possible way of bringing an actual environment as close as possible to the above-described assumption is that the user performs the motion of descending stairs. Observation data obtained through the user descending stairs can be used as observation data of the above-described prescribed walking state.

Since it is difficult to remove the difference between the above-described assumption and an actual environment completely, influence of the difference between the above-described assumption and an actual environment is reduced by using the correction factor K to measure the body weight of the user accurately according to Equation (1), in the present embodiment.

Upon completion of the computation of the body weight M, the control unit 41 terminates the body weight computation process. When the control unit 41 terminates the body weight computation process in S440 and advances to S450, the control unit 41 determines whether the body weight M of the user computed in the body weight computation process is within a normal range. The normal range can be determined in advance on the basis of a range corresponding to possible human body weights. In S450, the control unit 41 may determine that the body weight M of the user computed this time is not within the normal range when the difference between the body weight M and the body weight displayed for the user last time in S360 is greater than or equal to a threshold. The threshold can be determined to be the upper limit of the amount of change corresponding to the possible amount of change in body weight from the last time when the body weight was displayed up to this time. The threshold may be a fixed value or a variable value based on the time period that has elapsed since the last time when the body weight was displayed.

When the control unit 41 determines that the computed body weight M of the user is not within the normal range (No in S450), the control unit 41 discards the computed value of the body weight M, controls the display 53 so as to cause the display 53 to display, for a prescribed time period, an error message indicating that the measurement was unsuccessful and hence measurement is to be performed again (S470), and then advances to S410.

In contrast, when the control unit 41 determines that the computed body weight M of the user is within the normal range (Yes in S450), the control unit 41 advances to S460, temporarily stores the computed body weight M in the memory 415 as a measurement value, and terminates the computation control process.

Upon termination of the computation control process in S330, the control unit 41 determines whether there is a set number of measurement values temporarily stored in the memory 415 (S340), and when the control unit 41 determines that the number of stored measurement values is smaller than the set number (No in S340), the control unit 41 returns to S330. In this way, the control unit 41 repeatedly carries out the operation in S330 until the number of stored measurement values reaches the set number. Any number greater than or equal to one can be set as the set number.

When the set number of measurement values are stored (Yes in S340), the control unit 41 performs statistical processing on the set number of stored measurement values, to thereby compute a representative value of the measurement values, in S350. Specifically, the control unit 41 can compute the average value of the stored measurement values as the above-described representative value. Note that the representative value may be the median of the stored measurement values or the intermediate value of the greatest value and the smallest value among the stored measurement values.

When the representative value is computed in S350, the control unit 41 advances to S360 and controls the display 53 to cause the display 53 to display the computed representative value as a body weight value. The control unit 41 thereafter returns to S320.

Upon another input of an operation signal instructing to start measurement via the operation unit 55 after the returning to S320 (Yes in S320), the control unit 41 advances to S330. Upon input of an operation signal other than the above from the operation unit 55 (Yes in S325), the control unit 41 carries out the process corresponding to the instruction from the user on the basis of the operation signal (S370 to S390).

Specifically, upon input of a termination instruction from the user (Yes in S370), the control unit 41 terminates the connection with the shoe-type wearable device 20 and terminates the measurement display process. When the instruction from the user is not a termination instruction (No in S370), the control unit 41 carries out the process corresponding to the instruction (S390) and then returns to S320 to enter an operation waiting state.

According to the present embodiment described above, the pressure-sensitive sensor 31 made mainly of conductive rubber is provided to the shoe 10, and the body weight of the user is measured on the basis of an output from the pressure-sensitive sensor 31 and an output from the acceleration sensor 33. Unlike existing hard load cells, this pressure-sensitive sensor 31 has flexibility, which principally prevents decrease of wearing comfort of the shoe 10 even when the pressure-sensitive sensor 31 is arranged under the shoe insole 101 of the shoe 10. However, it is difficult to accurately measure the body weight of the user only on the basis of output from this pressure-sensitive sensor 31. To address this, in the present embodiment, the body weight of the user is measured in the above-described method by the use of an output from the acceleration sensor 33 together with an output from the pressure-sensitive sensor 31.

Hence, according to the present embodiment, it is possible to provide a highly-convenient body weight measurement system. Existing scales with a built-in load cell are substantially not portable for users, and therefore a user needs to move to a place where a scale is placed, in order to measure his/her body weight. In contrast to this, according to the present embodiment, the user can measure his/her body weight at any place at any desired timing as long as the user is wearing the shoes 10. Moreover, the user can acquire his/her body weight by performing simple walking movement without the necessity of standing still during the body weight measurement. Hence, according to the present embodiment, it is possible to perform body weight measurement with few restrictions in terms of time and place compared to existing body weight measurement and consequently to provide a highly convenient body weight measurement system. Such convenience makes it easier for the user to continuously measure his/her body weight. Hence, the measurement system 1 according to the present embodiment is useful for the user to track increase/decrease of his/her body weight and contributes to health care.

In addition, in the present embodiment, the body weight M is computed on the basis of observation data of a time period in which appropriate body weight measurement is possible on the basis of the change in acceleration. Hence, the body weight M can be computed at accuracy within a sufficiently practical range. Further, a measurement value of the body weight M is obtained a plurality of times, and a representative value (for example, the average value) obtained by performing statistical processing on the measurement values is displayed for the user as a measured body weight value. This reduces the influence of errors in measurement and enables a highly accurate measured body weight value to be displayed for the user. Note that "highly accurate" mentioned in association with the measurement system in this description means that the accuracy of a measured body weight value is within a practical range or that the accuracy is relatively high among a plurality of illustrative embodiments of the present disclosure, and does not necessarily mean that the accuracy is higher than other measurement techniques. From some test results, the measured body weight values obtained according to the present embodiment were within an error range of several percent from the true value.

The correspondence relationship between the terms of the present disclosure is as follows. The pressure-sensitive sensor 31 corresponds to an example of a force sensor. The functions provided by the operations in S330 to S350 performed by the control unit 41 correspond to an example of functions provided by an arithmetic unit. The function of the control unit 41 performing S310 to receive a detected force signal and a detected acceleration signal from the shoe-type wearable device 20 corresponds to an example of a function provided by an input unit. The function provided by the operation in S360 performed by the control unit 41 corresponds to an example of a function provided by an output unit. The function provided by the operation in S430 performed by the control unit 41 corresponds to an example of a function provided by an instruction unit.

Measurement systems according to a second embodiment to eighth embodiment to be described below are modified examples of the above-described measurement system 1 according to the first embodiment. For this reason, in the explanation of a measurement system according to each of the second to eighth embodiments, explanation of parts having the same configurations as those of the measurement system 1 according to the first embodiment among the parts of the measurement system of the embodiment is appropriately omitted. The components to which the same reference signs as those of the measurement system 1 of the first embodiment are attached in the measurement system of each of the second to eighth embodiments may be understood as the same components as those in the first embodiment in terms of hardware configuration. The software configuration of each of the parts to which the same reference sign is attached may be understood as having the same basic configuration as that of the first embodiment unless otherwise provided with explanation of an alternative process.

Second Embodiment

A measurement system 2 according to the second embodiment is different from the measurement system 1 of the first embodiment in that some of the processes carried out by the mobile communication terminal 40 in the first embodiment are carried out by a server device 60 connected to the mobile communication terminal 40 so as to be able to communicate with the mobile communication terminal 40, but is otherwise basically the same as the measurement system 1 of the first embodiment.

Figure 8:
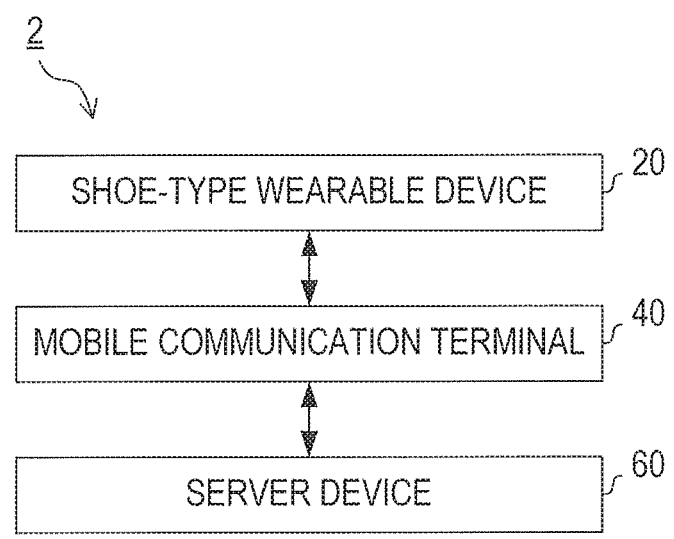
FIG. 8 is a diagram illustrating a configuration of a measurement system according to a second embodiment.

As illustrated in FIG. 8, the measurement system 2 of the second embodiment includes, as its constitution elements, the server device 60 capable of communicating with the mobile communication terminal 40, in addition to the shoe-type wearable device 20 and the mobile communication terminal 40.

The server device 60 carries out, for example, the operations indicated by broken lines in FIG. 4, instead of the mobile communication terminal 40. Specifically, the server device 60 acquires, from the mobile communication terminal 40, a detected force signal and a detected acceleration signal that the mobile communication terminal 40 has received from the shoe-type wearable device 20, sequentially or every certain time period. The server device 60 then computes the body weight M of the user on the basis of the detected force signals and the detected acceleration signals acquired from the mobile communication terminal 40 and transmits the representative value of the calculated body weight M (S350) to the mobile communication terminal 40. The server device 60 is capable of sequentially transmitting and receiving necessary data to and from the mobile communication terminal 40, in order to perform operations equivalent to S330 to S350 in the first embodiment.

The mobile communication terminal 40 can perform the following operations instead of the operations in S330 to S350. Specifically, the mobile communication terminal 40 can transfer, to the server device 60, the detected force signals and the detected acceleration signals received from the shoe-type wearable device 20, receive the representative value of the body weight M computed by the server device 60 on the basis of the transferred signals, and control the display 53 to cause the display 53 to display the received representative value as a body weight measurement value in S360. According to the second embodiment, it is possible to produce meaningful effects similar to those of the first embodiment in contrast to the related art.

Third Embodiment

Figure 6:
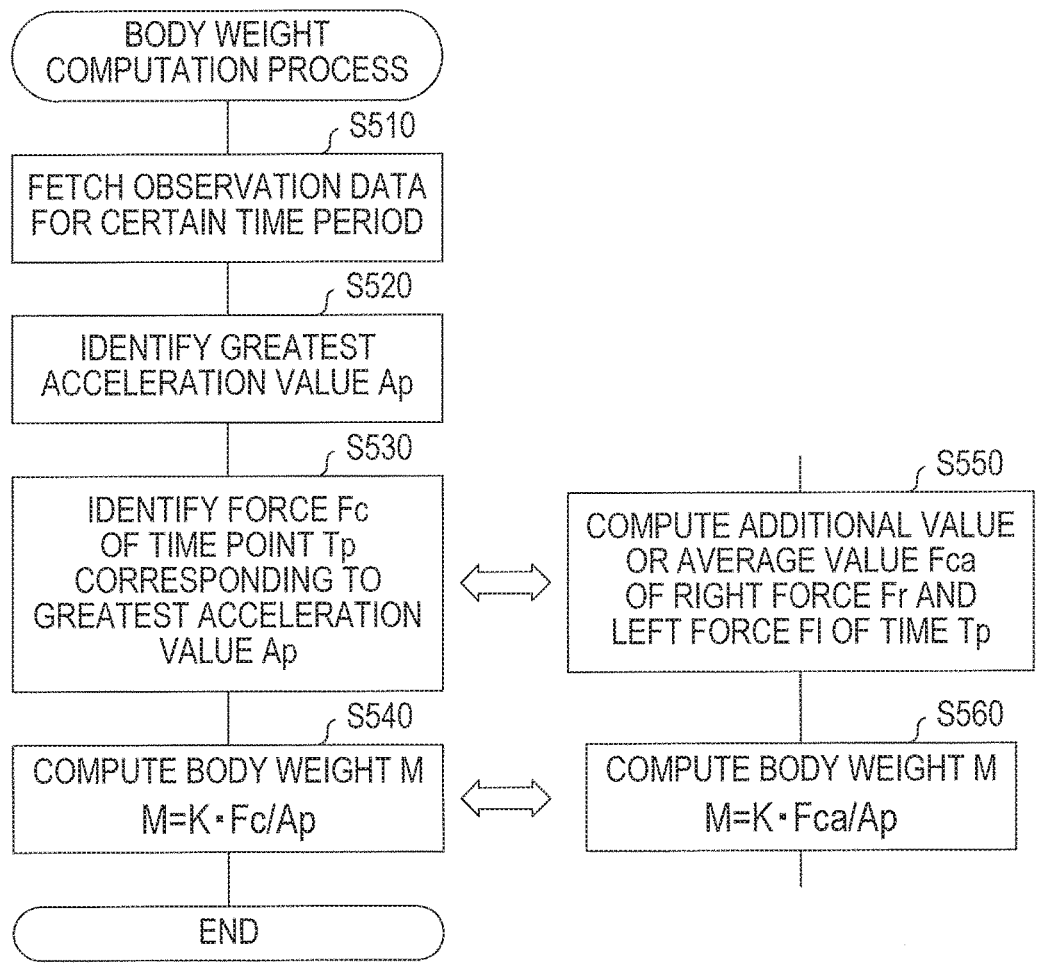
FIG. 6 is a flowchart illustrating a body weight computation process carried out by the control unit of the mobile communication terminal.
Figure 9:
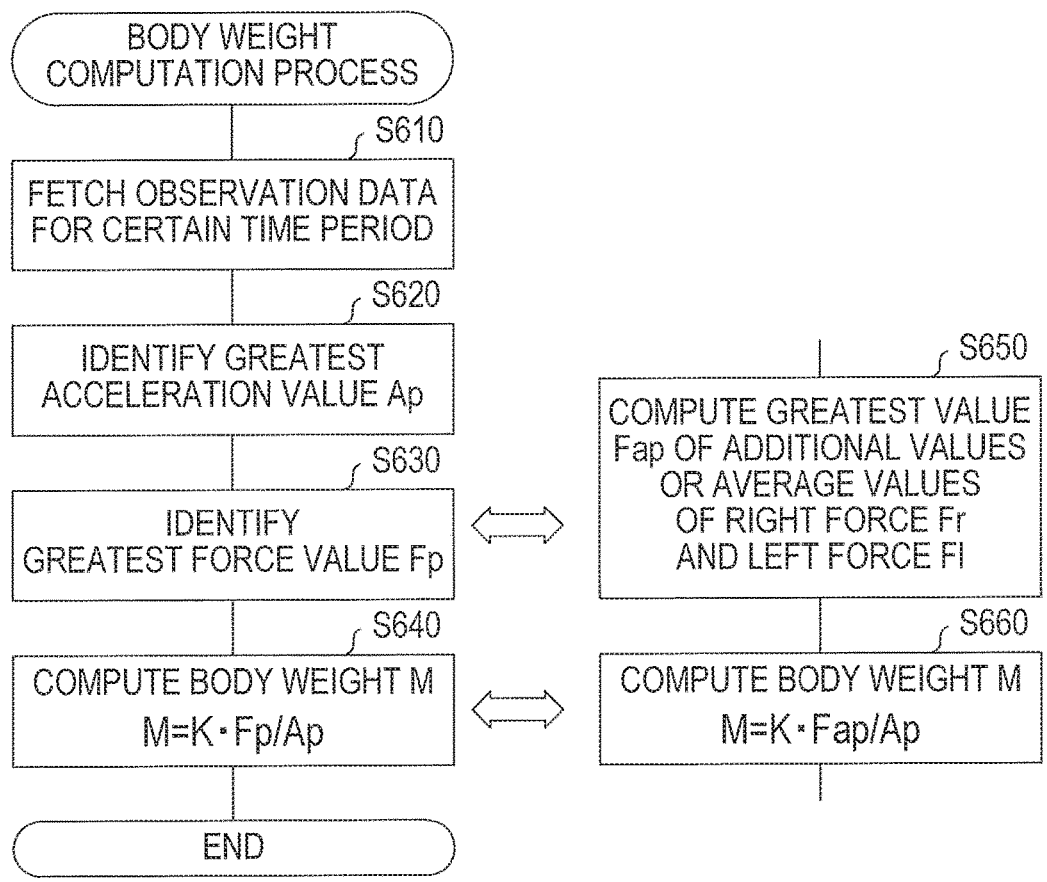
FIG. 9 is a flowchart illustrating a body weight computation process in a measurement system according to a third embodiment.

The measurement system of the third embodiment is different from the measurement system 1 of the first embodiment in that the control unit 41 of the mobile communication terminal 40 performs a body weight computation process presented in FIG. 9 in S440 instead of the body weight computation process presented in FIG. 6, but is otherwise basically the same as the measurement system 1 of the first embodiment in terms of the other respects.

Upon start of the body weight computation process presented in FIG. 9, the control unit 41 fetches observation data in S610 and S620 as in the operations in S510 and S520 and identifies the greatest acceleration value Ap in an observation period on the basis of the fetched observation data.

Subsequently, in S630, the control unit 41 identifies the greatest detected force value Fp in the observation period on the basis of the above-described observation data. In the first embodiment, the detected force value Fc of the time point Tp at which the greatest acceleration value Ap is detected is identified. However, in the present embodiment, the greatest detected force value Fp is identified independent of the greatest acceleration value Ap.

Depending on the kind of the pressure-sensitive sensor 31, the time required from when the force acts on the pressure-sensitive sensor 31 to when the acted force is reflected to an output of the pressure-sensitive sensor 31 is long in some case. When the degree of difference in delay time until the physical action is reflected to a detection value is too large to ignore between the pressure-sensitive sensor 31 and the acceleration sensor 33, it is possible to roughly identify the acceleration value Ap and the detected force value Fp at the time when the same event occurs, by identifying the greatest detected force value Fp as in the present embodiment.

Upon completion of the operation in S630, the control unit 41 computes the body weight M of the user according to Equation (2) below (S640).

$$M = K^* Fp/Ap \qquad \text{Equation (2)}$$

As in the first embodiment, the correction factor K can be obtained by substituting, into Equation (2), a pair of the greatest acceleration value Ap and the greatest detected force value Fc (Ap, Fc) obtained in the above-described walking state in an environment where the body weight M is known, together with the known body weight M. After the computation of the body weight M according to Equation (2) (S640), the control unit 41 terminates the body weight computation process presented in FIG. 9 and advances to S450 (refer to FIG. 5).

According to the measurement system of the third embodiment described above, even when the difference in time delay until a physical action is reflected to a detection value is large between the pressure-sensitive sensor 31 and the acceleration sensor 33, it is possible to compute the body weight M appropriately.

Fourth Embodiment

Figure 10:
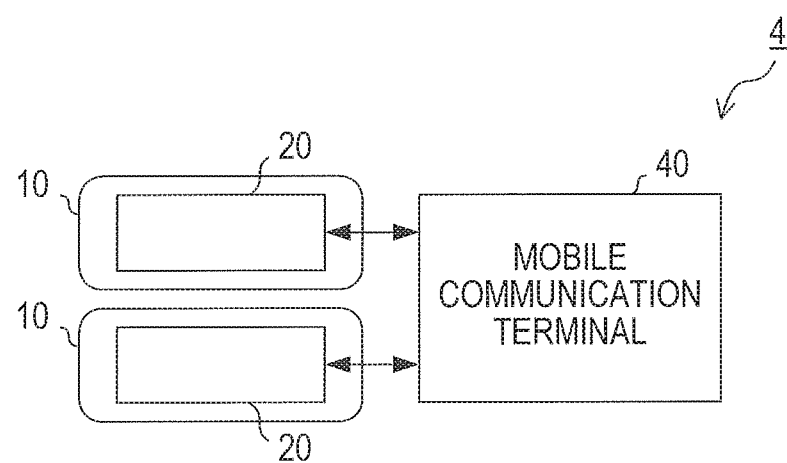
FIG. 10 is a diagram illustrating a configuration of a measurement system according to a fourth embodiment.

A measurement system 4 of the fourth embodiment is a system configured so that the shoe-type wearable device 20 is installed in each of the paired shoes 10 to be put on both feet as illustrated in FIG. 10 and the mobile communication terminal 40 receives detected force signals from the two shoe-type wearable devices 20 corresponding to both feet to compute the body weight M.

In S310 (FIG. 4), the control unit 41 of the mobile communication terminal 40 establishes a connection with each of the shoe-type wearable devices 20 corresponding to both feet and registered in advance and starts to receive detection signals transmitted from the shoe-type wearable devices 20. Further, the control unit 41 computes the average of detected acceleration values (L2 norms) of the respective feet, to use the average value for the determination of a motion state of the user (S410) and the computation of the greatest acceleration value Ap (S520). Alternatively, the control unit 41 receives detected acceleration signals only from one of the shoe-type wearable devices 20 of both feet and carries out the operations in S410 and S520 as in the first embodiment on the basis of the detected acceleration signals.

The control unit 41 of the present embodiment can carry out the operations in S550 and S560 presented in a right-hand area in FIG. 6, instead of S530 and S540, in the body weight computation process (S440).

In S550, the control unit 41 can compute the additional value or the average value of the detected force values Fr and Fl of the time point Tp at which the greatest acceleration value Ap is detected, as a detected force value Fca to be used for the computation of the body weight M. The detected force value Fr here represents the detected force value of the time point Tp indicated by a detected force signal obtained from the pressure-sensitive sensor 31 included in the shoe-type wearable device 20 of the right foot, and the detected force value Fl represents the detected force value of the time point Tp indicated by a detected force signal obtained from the pressure-sensitive sensor 31 included in the shoe-type wearable device 20 of the left foot.

In S560, the control unit 41 computes the body weight M of the user according to Equation (3) below.

$$M=K*Fca/Ap \quad \text{Equation (3)}$$

The correction factor K can be obtained by substituting, into Equation (3), a pair of the greatest acceleration value Ap and the corresponding detected force value Fca (Ap, Fca) obtained in an environment where the body weight M is known, together with the known body weight M, in a similar manner as in the first embodiment. The values K*Fca obtained when the additional value and the average value of the detected force values Fr and Fl are adopted as the detected force value Fca result in being substantially the same. After the computation of the body weight M according to Equation (3), the control unit 41 terminates the body weight computation process and advances to S450 (refer to FIG. 5).

According to the present embodiment, the shoe-type wearable devices 20 are installed for both feet, which makes it possible to reduce influence of the variation in load between right and left and to thereby compute the body weight M highly accurately. Note that the control unit 41 may be configured to sequentially perform the operations in S610, S620, S650, and S660 presented in FIG. 9, in the body weight computation process (S440).

In S650, the control unit 41 can identify the greatest value Fap of the additional value or the average value of the detected force values Fr and Fl in the observation period on the basis of observation data. In S660, the control unit 41 can compute the body weight M of the user according to Equation (4) below.

$$M=K*Fap/Ap \quad \text{Equation (4)}$$

The body weight computation of this method is useful when the difference in time delay until a physical action is reflected to a detection value is large between the pressure-sensitive sensor 31 and the acceleration sensor 33, as in the third embodiment.

When the pressure-sensitive sensor 31 is provided in each of both feet, it is possible to measure the body weight M highly accurately on the basis of outputs from the pressure-sensitive sensors 31 of both feet without guiding the motion state of the user so that the pressure-sensitive sensor 31 of one of the feet is to bear the total body weight. The control unit 41 may be configured to lead the user to jump with both feet and to make determination about the state in which the user is jumping as the motion state of the user, in S410 and S420. The control unit 41 may be configured to fetch observation data obtained during the motion of the user repeating jumping with both feet and to compute the body weight M.

Fifth Embodiment

Figure 11:
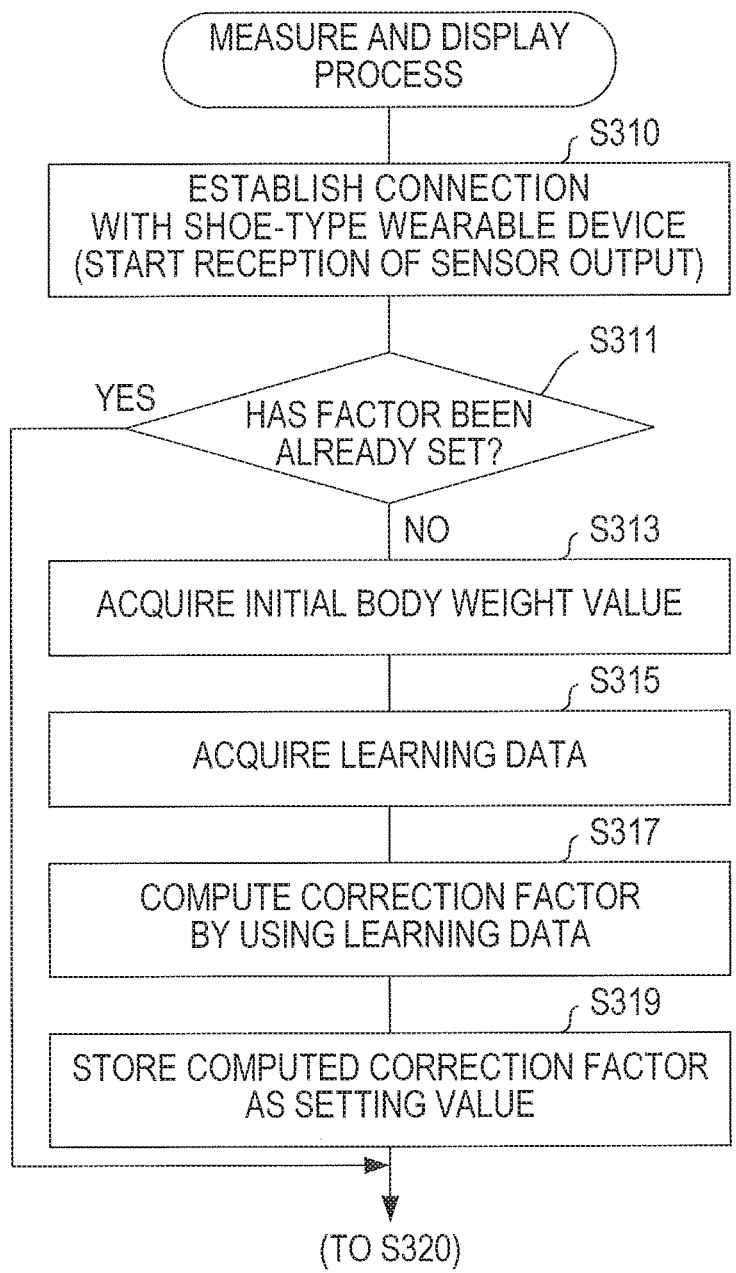
FIG. 11 is a flowchart illustrating part of a measurement and display process in a measurement system according to a fifth embodiment.

The measurement system of the fifth embodiment is configured such that the control unit 41 of the mobile communication terminal 40 performs the operations in S310 to S319 presented in FIG. 11 before advancing to S320 (refer to FIG. 4) to set the correction factor K based on an initial body weight value M0 acquired from the user. The control unit 41 of the present embodiment starts the measurement and display process presented in FIG. 11, instead of the measurement and display process presented in FIG. 4, and after performing the operations in S310 to S319, performs the operations in S320 and the subsequent steps presented in FIG. 4 as in the first embodiment. Note that the correction function K used in S540 (refer to FIG. 6) is the correction function K set in S319 and stored in the memory 415.

Upon start of the measurement and display process presented in FIG. 11, the control unit 41 establishes a connection with the shoe-type wearable device 20, and starts to receive detection signals transmitted from the shoe-type wearable device 20 (S310). The control unit 41 thereafter determines whether the correction function K is set (S311), and when determining that the correction function K is not set (No in S311), advances to S313, while, when determining that the correction function K is set (Yes in S311), advances to S320.

The control unit 41 determines No in S311 when the operations in S313 and the subsequent steps are not performed in the past and no correction factor K is thus stored in the memory 415. Unlike the first embodiment, in the measurement system of the present embodiment, the value of the correction factor K is not described in the above-described dedicated program executing the measurement and display process, and hence setting of the correction factor K is necessary in order to perform body weight measurement.

In S313, the control unit 41 causes the display 53 to display an initial value input window for acquiring information on the initial body weight value M0 from the user. Upon input of the information on the initial value M0 from the user via the operation unit 55, the control unit 41 advances to S315. The user can measure his/her body weight by using another scale to input the initial value M0.

In S315, the control unit 41 carries out a process of acquiring a plurality of pieces of learning data. For the acquisition of the plurality of learning data, the control unit 41 can repeatedly perform operations similar to those in S410 to S440 (refer to FIG. 5), a plurality of times in S315. Specifically, the control unit 41 can repeatedly perform, as the above-described similar operations, the same operations as those in S410 to S430 a plurality of times, thereafter in S440, performs the operations in S510 to S530 presented in FIG. 6, and thereafter stores, in the memory 415, the pair of the greatest acceleration value Ap and the detected force value Fc identified in S520 and S530, instead of the operation in S540, together with the above-described input information on the initial value M0, as learning data (Ap, Fc, M0).

The control unit 41 thereafter advances to S317, inputs the values Ap, Fc, and M0 indicated by each of the pieces of learning data, into Equation (1), and computes a group of correction functions K corresponding to the respective pieces of learning data. Further, the control unit 41 performs statistical processing on the group of correction functions K to compute a setting value of the correction function K. Specifically, as the statistical processing, the control unit 41 can carry out a process of computing the average value of the correction functions K. The control unit 41 stores the setting value of the correction function K thus computed, in the memory 415, to set the correction function K (S319). Specifically, the control unit 41 can compute the average value of the above-described group of correction functions K (S317) and stores the computed average value as the setting value of the correction function K, in the memory 415 (S319). The setting value is stored in the NVRAM included in the memory 415 for a long time period.

After the operation in S319, the control unit 41 advances to S320 (refer to FIG. 4) and performs an operation similar to that in the first embodiment. Specifically, the control unit 41 computes the body weight M on the basis of the correction function K stored in the memory 415.

According to the above-described measurement system of the present embodiment, the correction function K is computed on the basis of the information on the initial body weight value M0 obtained from the user and the information on the values Ap and Fc obtained from the observation data relating to the user. Hence, it is possible to measure the body weight M by the use of the correction function K to which the tendency of the user in terms of walking action is reflected. Hence, according to the present embodiment, it is possible to measure body weight further accurately.

The correspondence relationship between the terms of the present embodiment is as follows. The function provided by the operation in S313 performed by the control unit 41 corresponds to an example of a function provided by an acquisition unit. The function provided by the operations in S315 to S319 performed by the control unit 41 corresponds to an example of a function provided by an initial processing unit.

Sixth Embodiment

Figure 12:
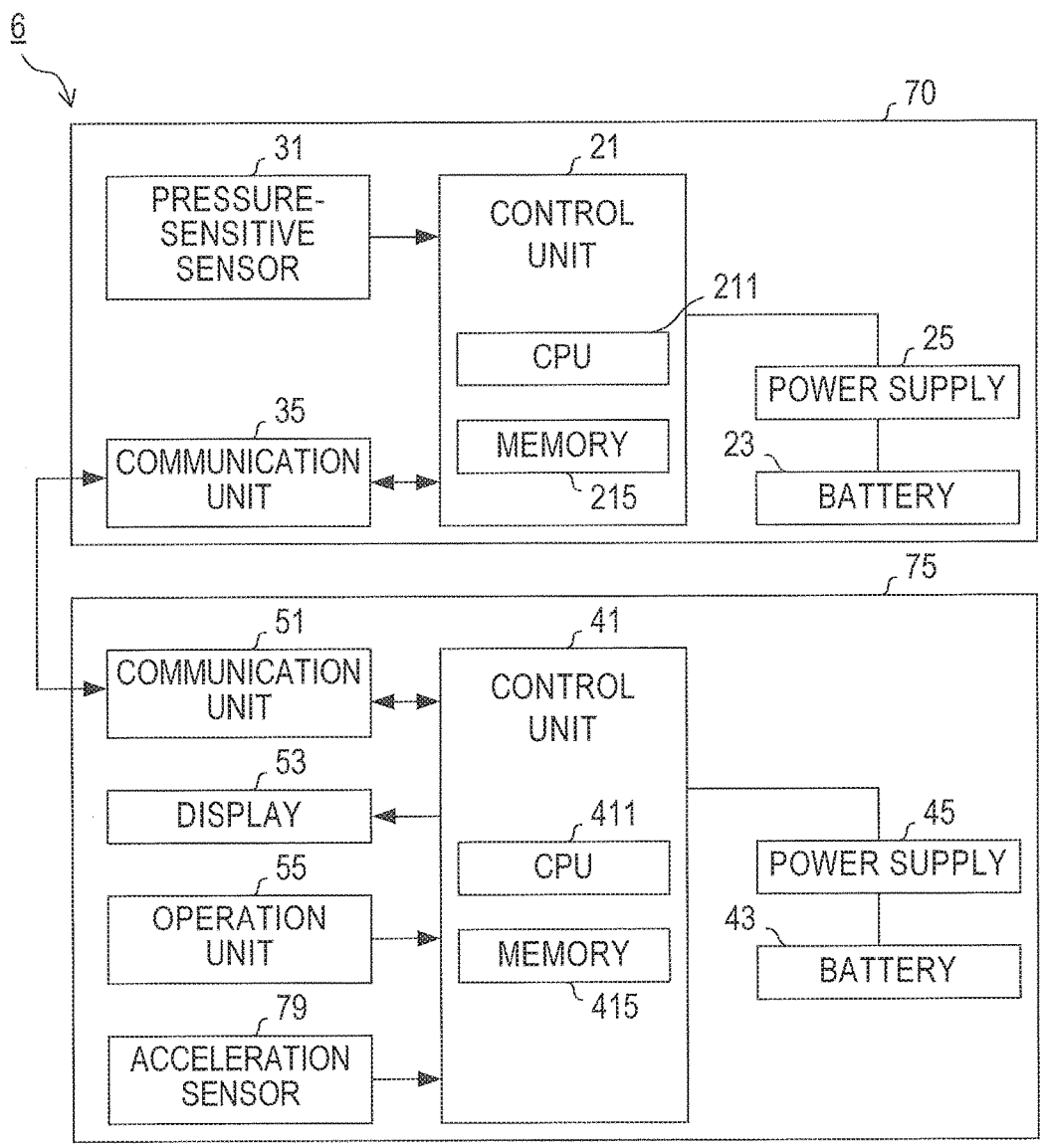
FIG. 12 is a block diagram illustrating a configuration of a measurement system according to a sixth embodiment.

A measurement system 6 of the sixth embodiment is a system that carries out similar processes as those in the measurement system 1 of the first embodiment by the cooperation between a shoe-type wearable device 70, which does not include any acceleration sensor, and a mobile communication terminal 75, which includes an acceleration sensor 79, as illustrated in FIG. 12.

As illustrated in FIG. 12, the shoe-type wearable device 70 of the present embodiment has the same hardware configuration as that of the shoe-type wearable device 20 of the first embodiment except that the shoe-type wearable device 70 does not include any acceleration sensor. A control unit 21 of the shoe-type wearable device 70 carries out the process presented in FIG. 3 as in the first embodiment and after the establishment of a connection with the mobile communication terminal 75, continuously transmits detected force signals from the pressure-sensitive sensor 31 to the mobile communication terminal 75 until the connection is terminated. Note that no detected acceleration signal is transmitted to the mobile communication terminal 75.

Meanwhile, the mobile communication terminal 75 of the present embodiment is configured to include the acceleration sensor 79 in addition to the same hardware configuration as that of the mobile communication terminal 40 of the first embodiment. The acceleration sensor 79 may have the same configuration as that of the acceleration sensor 33 of the first embodiment or may have a different configuration. Examples of the mobile communication terminal 75 include a smartphone. Smartphones that are currently commercially available often include an acceleration sensor.

The control unit 41 of the mobile communication terminal 75 carries out a similar measurement and display process as that by the control unit 41 of the first embodiment, by the use of acceleration detection signals acquired from the acceleration sensor 79 of the mobile communication terminal 75. According to the measurement system 6 of the present embodiment, it is not necessary to provide any acceleration sensor to the shoe-type wearable device 20, which makes easier to manufacture the shoe-type wearable device 70 that is inexpensive and small in size. However, the mobile communication terminal 75, such as a smartphone, may be away from the body of the user. In view of this, the control unit 41 may be configured to perform an operation of causing the display 53 to display a message instructing the user to carry the mobile communication terminal 75 so that the mobile communication terminal 75 follows a walking action, at the timing of advancing to S330 (refer to FIG. 4) in response to measurement start operation. A similar message may be displayed on the display 53 in S430 and S470.

Seventh Embodiment

The measurement system of the seventh embodiment is a system in which the functions of the mobile communication terminal 40 computing the body weight M and computing a representative value in the first embodiment are provided to the shoe-type wearable device 20. Hence, the hardware configuration of the measurement system of the seventh embodiment is the same as the hardware configuration of the measurement system 1 of the first embodiment.

Figure 13:
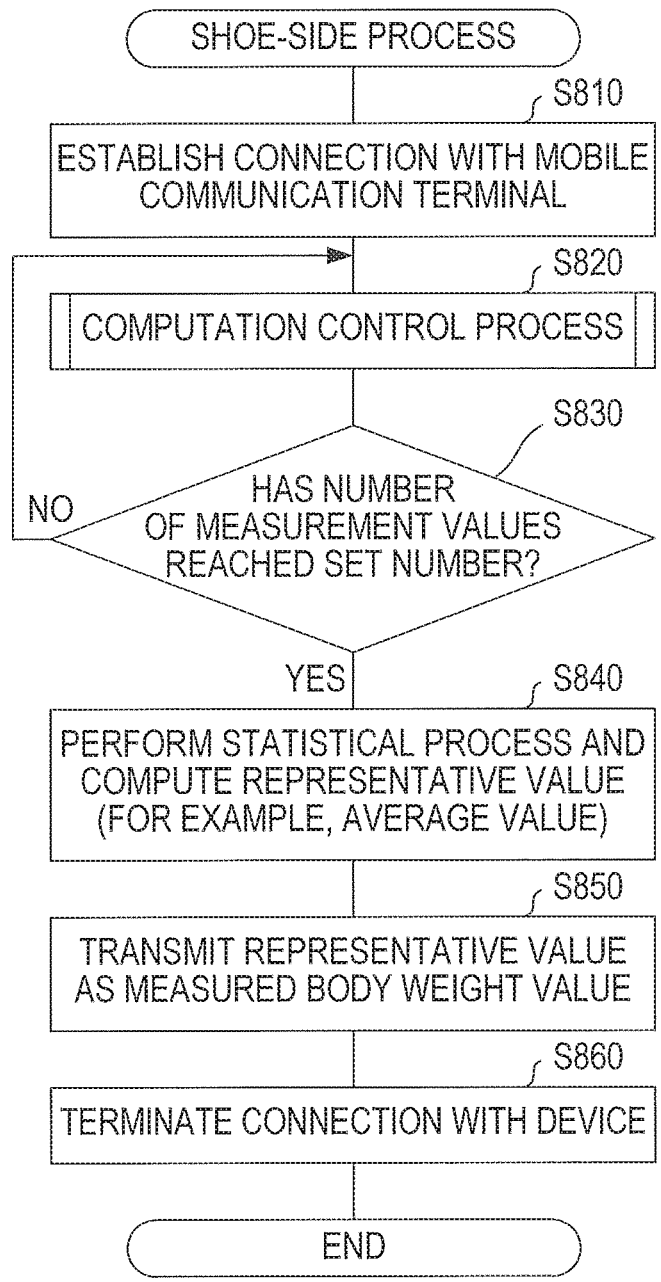
FIG. 13 is a flowchart illustrating a shoe-side process in a measurement system according to a seventh embodiment.

Meanwhile, the control unit 21 of the shoe-type wearable device 20 is configured to carry out a shoe-side process presented in FIG. 13, instead of the shoe-side process illustrated in FIG. 3. Upon start of the shoe-side process in FIG. 13, after the establishment of a connection with the mobile communication terminal 40 (S810), the control unit 21 carries out, in S820, a computation control process similar to that in the first embodiment (refer to FIG. 5).

Note that the control unit 21 carries out the computation control process on the basis of detected force signals from the pressure-sensitive sensor 31 of the shoe-type wearable device 20 and detected acceleration signals from the acceleration sensor 33 of the shoe-type wearable device 20. Since the shoe-type wearable device 20 does not include any display, in S430 and S470, the control unit 21 transmits a signal instructing display of a corresponding message to the mobile communication terminal 40 via the communication unit 35.

The control unit 21 carries out the computation control process in S820 repeatedly until a set number of measurement values are stored in the memory 215 through the operation in S460 (refer to FIG. 5). When the set number of measurement values are stored (Yes in S830), the control unit 21 computes a representative value of the measurement values as in S350 by performing statistical processing on the stored set number of measurement values (S840). The control unit 21 then transmits a signal that includes the computed representative value and that instructs display of the representative value as a measured body weight value, to the mobile communication terminal 40 via the communication unit 35 (S850). The control unit 21 then terminates the connection with the mobile communication terminal 40 (S860) and terminates the process presented in FIG. 13.

Figure 14:
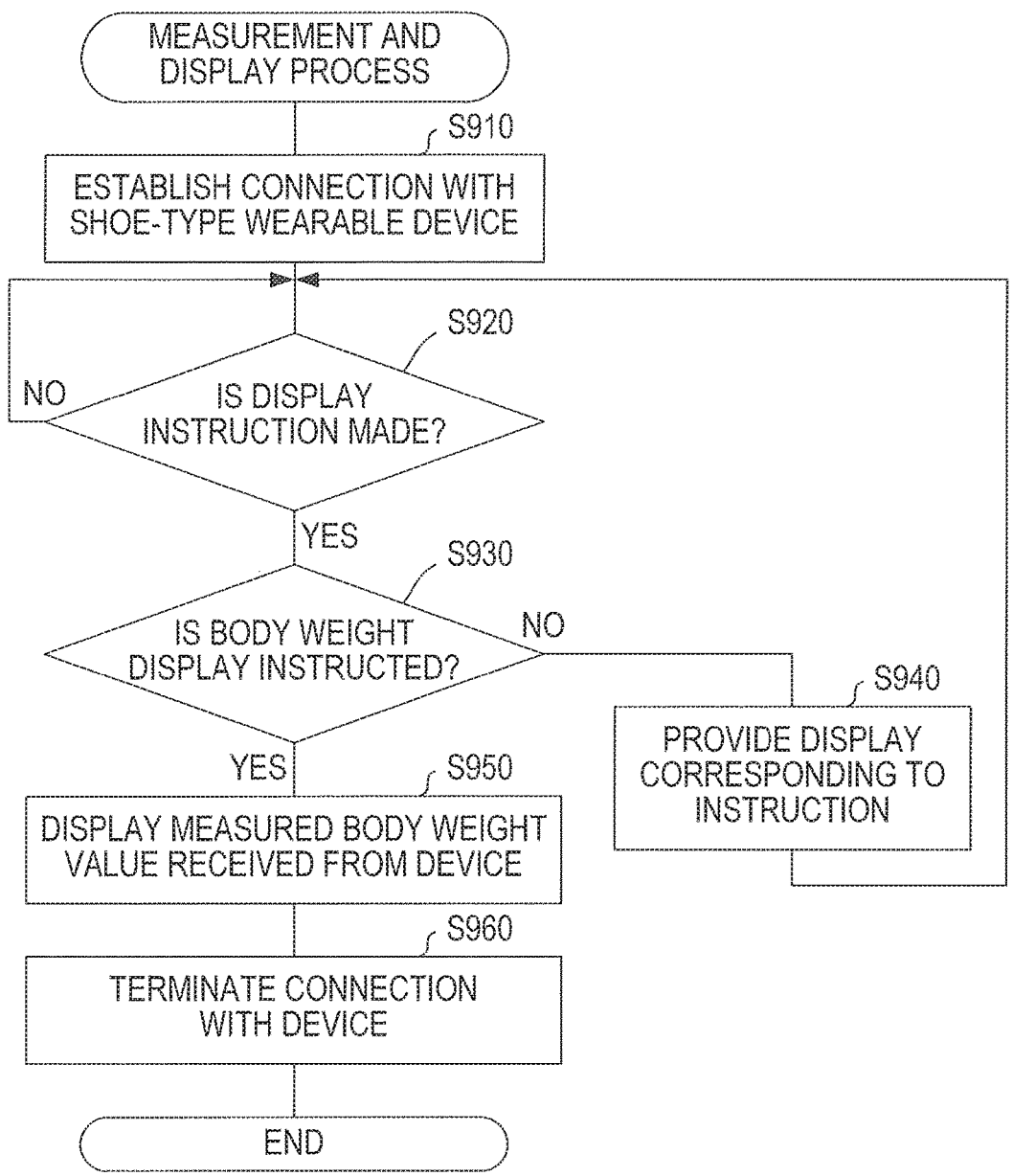
FIG. 14 is a flowchart illustrating a measurement and display process in the measurement system according to the seventh embodiment.

Meanwhile, the control unit 41 of the mobile communication terminal 40 is configured to carry out the measurement and display process presented in FIG. 14, instead of the measurement and display process presented in FIG. 4.

Upon start of the measurement and display process, the control unit 41 establishes a connection with the shoe-type wearable device 20 (S910). The control unit 41 then stands by until receiving a display instruction from the shoe-type wearable device 20, and performs, upon receipt of a display instruction (Yes in S920), an operation corresponding to the received display instruction.

When the received display instruction is not an instruction to display a measured body weight value (No in S930), the control unit 41 controls the display 53 to cause the display 53 to display a message corresponding to the display instruction for the user (S940). The control unit 41 thereafter returns to S920. In S940, specifically, a message similar to the message displayed in the display 53 in S430 and S470 in the first embodiment is displayed according to a display instruction.

In contrast, upon receipt of an instruction to display a measured body weight value by execution of the operation in S850 in the shoe-type wearable device 20 (Yes in S930), the control unit 41 controls the display 53 to cause the display 53 to display the measured body weight value acquired from the shoe-type wearable device 20 (S950). The control unit 41 then terminates the connection with the shoe-type wearable device 20 (S960) and terminates the measurement and display process. The control unit 41 may record measured body weight values received from the shoe-type wearable device 20 in the memory 415, specifically, the NVRAM, in order for the user to be able to check the log of the measured body weight values.

As can be understood from the above-described seventh embodiment, the functions of the measurement system, in particular, the functions implemented by software, may be assigned to any of the shoe-type wearable device 20 and the mobile communication terminal 40. Further, the functions implemented by the measurement system 1 of the first embodiment may be aggregated in a shoe-type wearable device.

Eighth Embodiment

Figure 15:
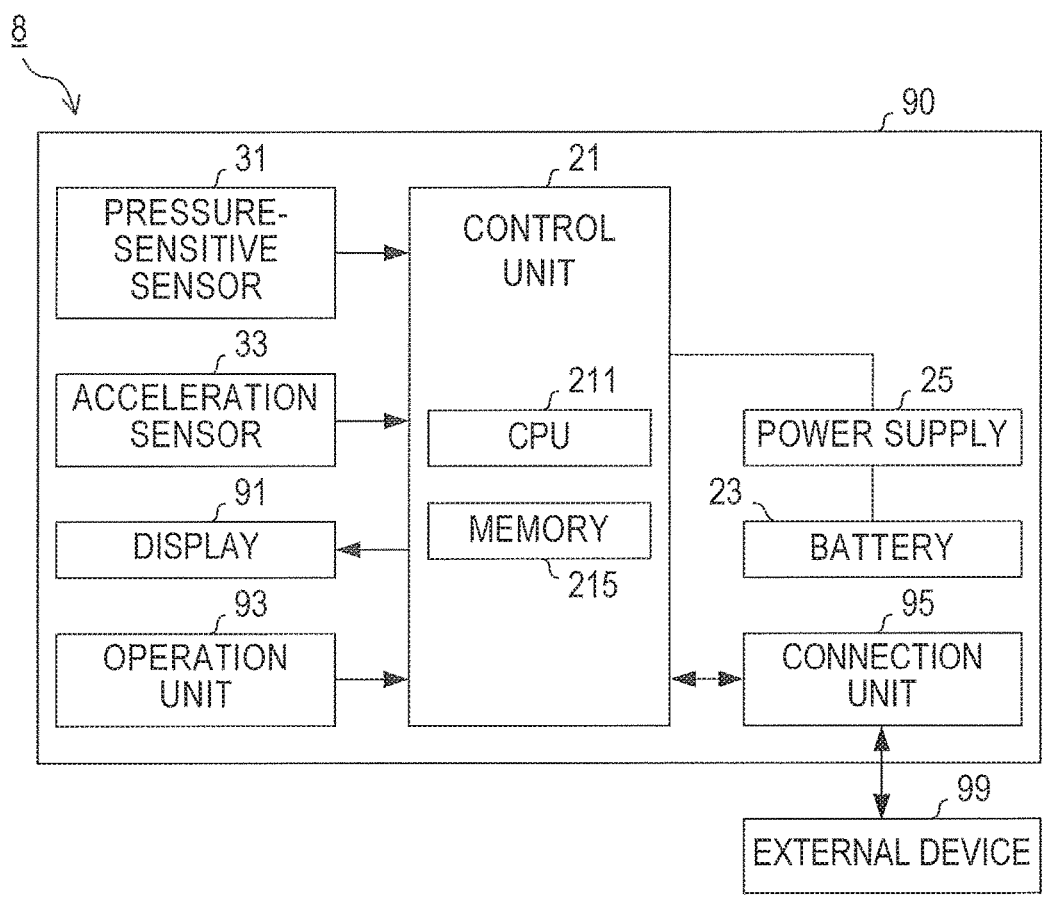
FIG. 15 is a block diagram illustrating a configuration of a measurement system according to an eighth embodiment.

The measurement system 8 of the eighth embodiment is a system in which all the functions of the measurement system 1 of the first embodiment are basically included in a shoe-type wearable device 90. As illustrated in FIG. 15, the shoe-type wearable device 90 of the present embodiment further includes, in addition to the configuration of the shoe-type wearable device 20 of the first embodiment, a display 91, an operation unit 93, and a connection unit 95.

The display 91 is provided to the main body case 201 so as to be able to display various messages and measured body weight values for the user. The operation unit 93 may be configured as a touch panel on the display 91 or may be provided to the main body case 201 as a different mechanical operation switch.

The connection unit 95 includes a connection port for the connection with an external device 99 and is configured to be able to communicate with the external device 99 to which the connection unit 95 is connected through the connection port. The connection unit 95 is configured, for example, by a universal serial bus (USB) interface.

Figure 16:
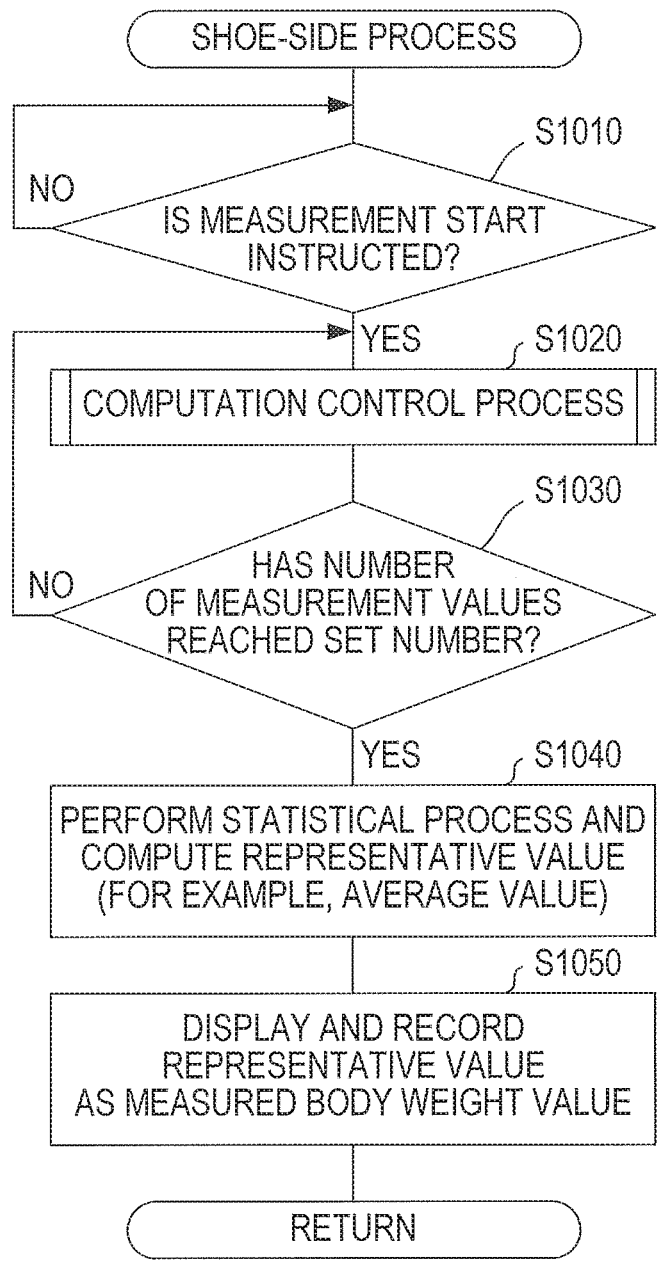
FIG. 16 is a flowchart illustrating a shoe-side process according to the eighth embodiment.

The control unit 21 of the shoe-type wearable device 90 according to the present embodiment is configured to repeatedly carry out a shoe-side process presented in FIG. 16, instead of the shoe-side process illustrated in FIG. 3.

Upon start of the process presented in FIG. 16, the control unit 21 stands by until a measurement start instruction is input from the user via the operation unit 93 (S1010). Upon input of the measurement start instruction (Yes in S1010), the control unit 21 carries out a computation control process (refer to FIG. 5) in S1020. The computation control process carried out in S1020 is similar to the computation control process carried out by the mobile communication terminal 40 in the first embodiment. Note that the destination of a message is the display 91 of the shoe-type wearable device 90.

The control unit 21 carries out the computation control process in S1020 repeatedly until the set number of measurement values are stored in the memory 215, and when the set number of measurement values are stored (Yes in S1030), the control unit 21 computes a representative value of the measurement values as in S350 by performing statistical processing on the stored set number of measurement values (S1040). The control unit 21 further controls the display 91 to cause the display 91 to display the computed representative value as a measured body weight value. The control unit 21 further records the computed represented value in the memory 215, specifically, the NVRAM (S1050).

The control unit 21 repeatedly carries out the above-described shoe-side process and thereby displays and records the measured body weight value based on detected acceleration signals from the acceleration sensor 33 and detected force signals from the pressure-sensitive sensor 31, every time a measurement start instruction is input.

Upon connection of the external device 99 to the connection unit 95 and request for output of log information by the external device 99, the control unit 21 operates so as to provide the above-described recorded measured body weight value as log information to the external device 99 connected to the connection unit 95. When the connection unit 95 is a USB interface, the shoe-type wearable device 90 can charge the battery 23 by the use of power from an external power supply connected via the USB interface.

According to the present embodiment, the shoe-type wearable device 90 can independently display a measured body weight value, which improves the convenience of the user who does not carry any portable communication terminal with him/her. As a modified example, the shoe-type wearable device 90 may be configured to store the log of measured body weight values in an external server device via cloud services.

Other Embodiments

The measurement systems of the first to eighth embodiments have been described above. However, the technique of the present disclosure is not limited to the first to eighth embodiments and may take various modes. For example, in the above-described embodiments, the configurations of the measurement systems in which the wearable device 20, 70, or 90 is installed in the shoe(s) have been described. However, this device may be installed in footwear, such as sandals, other than shoes, and may be installed in socks. Footwear here may be understood to include socks. The above-described technique of the present disclosure may be used for measurement of the body weights of animals other than human or may be used for measurement of weight other than body weight. The configuration of the technique of the present disclosure implementable by information processing based on a program may be provided by recording the corresponding program in a computer readable recording medium. Examples of the computer readable recording medium include, in addition to a semiconductor memory, various recording media such as an optical disk, a magnetic disk, and a magneto-optical disk.

The functions of a single one of the components in the above-described embodiments may be distributed among a plurality of components. The functions of a plurality of components may be integrated into a single component. Part of the configuration of any of the above-described embodiments may be omitted. At least part of the configuration of any of the above-described embodiments may be added to or substituted by the configuration of a different one of the above-described embodiments. Various modes within the technical spirit defined by the words described in the scope of claims are embodiments of the present disclosure.

What is claimed is:

1. A measurement system comprising:
   one or more force sensors arranged so as to receive impact generated by motion of a measurement target;
   an acceleration sensor arranged to detect acceleration of the measurement target;
   a processor configured to compute a weight of the measurement target, based on a ratio of a detected force value indicating a magnitude of force detected by the one or more force sensors to a detected acceleration value indicating acceleration detected by the acceleration sensor;

a display configured to display the computed weight; and a storage unit storing a correction factor for correcting the detected force value to a value indicating magnitude of force to be detected on an assumption that the force sensor has received entire weight of the measurement target;

wherein the processor computes, as the weight of the measurement target, a ratio of a corrected detected force value to the detected acceleration value, and the corrected detected force value corresponds to a value obtained by correcting the detected force value by using the correction value stored in the storage unit.

2. The measurement system according to claim 1, wherein the weight of the measurement target is body weight of a measurement target person, wherein the one or more force sensors are arranged so as to support the measurement target person and receive impact generated by motion of the measurement target person, and wherein the acceleration sensor is arranged so as to move together with the measurement target person.

3. The measurement system according to claim 2, wherein, the one or more force sensors include one or more force sensors arranged in a portion of footwear put on a foot of the measurement target person, the portion supporting the body weight of the measurement target person.

4. The measurement system according to claim 3, wherein the one or more force sensors are force sensors arranged in respective pieces of a pair of footwear put on both feet of the measurement target person.

5. The measurement system according to claim 2, wherein the processor is configured to determine that the measurement target person is walking based on at least one change in acceleration, and to compute the body weight based on the detected force value and the detected acceleration value when the measurement target person is walking.

6. The measurement system according to claim 1, wherein the processor computes the weight of the measurement target, based on the detected force value and the detected acceleration value in a period in which change of the detected acceleration value satisfies a prescribed condition.

7. The measurement system according to claim 1, wherein the processor computes the weight of the measurement target, based on a greatest value of the detected acceleration value in a period satisfying a prescribed condition and the detected force value indicating magnitude of force detected by the force sensor when the greatest value is detected or the greatest value of the detected force value in the period.

8. The measurement system according to claim 7, wherein the period satisfying the prescribed condition is a certain period after a measurement instruction is input via a user interface.

9. The measurement system according to claim 7, wherein the period satisfying the prescribed condition is a period after a measurement instruction is input via a user interface and is a certain period in which change of the detected acceleration value satisfies a prescribed condition.

10. The measurement system according to claim 7, wherein the processor is configured to instruct performing of a specific motion by the measurement target through the display, and wherein the period satisfying the prescribed condition is a period in which the specific motion is performed in response to the instruction.

11. The measurement system according to claim 1, wherein the processor is configured to compute a statistical representative value of the weight by performing statistical processing on a group of the weights computed by repeatedly carrying out a process of computing the weight, and wherein the processor is configured to display the representative value on the display.

12. The measurement system according to claim 1, comprising:

a mobile device; and a wearable device configured to communicate with the mobile device;

wherein the one or more force sensors and the acceleration sensor are provided in the wearable device;

wherein the processor and the display are provided in the mobile device; and wherein the processor is configured to acquire the detected force value and the detected acceleration value from the wearable device by communication with the wearable device.

13. The measurement system according to claim 1, comprising:

a mobile device; and a wearable device configured to communicate with the mobile device;

wherein the one or more force sensors are provided in the wearable device;

wherein the acceleration sensor, the processor, and the display are provided in the mobile device; and wherein the processor is configured to acquire the detected force value from the wearable device by communication with the wearable device.

14. A measurement system comprising:

one or more force sensors arranged so as to receive impact generated by motion of a measurement target;

an acceleration sensor arranged to detect acceleration of the measurement target;

a processor configured to compute a weight of the measurement target, based on a ratio of a detected force value indicating a magnitude of force detected by the one or more force sensors to a detected acceleration value indicating acceleration detected by the acceleration sensor;

a display configured to display the computed weight; and a storage unit storing a correction factor;

wherein the processor acquires an initial value of the weight of the measurement target, acquires a detected force value and detected acceleration value as learning data, computes the correction factor and stores the correction factor in the storage unit based on the initial value and the learning data, and computes, as the weight of the measurement target, a value obtained by applying the correction factor to the ratio.

15. A measurement system comprising:

one or more force sensors arranged so as to receive impact generated by motion of a measurement target;

an acceleration sensor arranged to detect acceleration of the measurement target;

a processor configured to compute a weight of the measurement target, based on a ratio of a detected force value indicating a magnitude of force detected by the one or more force sensors to a detected acceleration value indicating acceleration detected by the acceleration sensor; and a display configured to display the computed weight;

wherein the weight of the measurement target is body weight of a measurement target person;

wherein the one or more force sensors are arranged so as to support the measurement target person and receive impact generated by motion of the measurement target person;

wherein the acceleration sensor is arranged so as to move together with the measurement target person;

wherein the processor is configured to determine that the measurement target person is walking based on at least one change in acceleration, and to compute the body weight based on the detected force value and the detected acceleration value when the measurement target person is walking; and wherein computing the body weight comprises:
fetching the detected force value and the detected acceleration value for a certain time period;
identifying a greatest acceleration value (Ap) in the certain time period;
identifying a detected force value (Fc) of a time point (Tp) corresponding to the greatest acceleration value (Ap); and
computing the body weight (M) using the following equation:

$$M = K \cdot Fc/Ap$$

wherein K is an experimentally derived correction factor.

16. The measurement system according to claim 15, wherein computing the body weight comprises:
acquiring a known initial body weight of the measurement target person;
acquiring a plurality of pairs of the greatest acceleration value (Ap) and the corresponding detected force value (Fc) when the measurement target person is walking as learning data;
computing K by using the learning data; and
storing K for use in computing the body weight (M).

* * * * *